United States Patent
Takaki et al.

(10) Patent No.: US 12,307,618 B2
(45) Date of Patent: May 20, 2025

(54) INFORMATION PROCESSING APPARATUS AND INFORMATION PROCESSING METHOD FOR ALIGNING A SECOND VIRTUAL OBJECT WITH A FIRST VIRTUAL OBJECT

(71) Applicant: SONY GROUP CORPORATION, Tokyo (JP)

(72) Inventors: Goro Takaki, Tokyo (JP); Matthew Forrest, Tokyo (JP); Shusuke Eshita, Tokyo (JP); Kenzo Nakajima, Tokyo (JP); Yo Nonoyama, Tokyo (JP); Satoshi Akagawa, Tokyo (JP); Katsuji Miyazawa, Tokyo (JP); Keisuke Ito, Tokyo (JP); Shoji Watanabe, Tokyo (JP)

(73) Assignee: SONY GROUP CORPORATION, Tokyo (JP)

( * ) Notice: Subject to any disclaimer, the term of this patent is extended or adjusted under 35 U.S.C. 154(b) by 154 days.

(21) Appl. No.: 17/921,709

(22) PCT Filed: Apr. 30, 2021

(86) PCT No.: PCT/JP2021/017146
§ 371 (c)(1),
(2) Date: Oct. 27, 2022

(87) PCT Pub. No.: WO2021/230101
PCT Pub. Date: Nov. 18, 2021

(65) Prior Publication Data
US 2023/0162458 A1    May 25, 2023

(30) Foreign Application Priority Data
May 13, 2020  (JP) .................................. 2020-084483

(51) Int. Cl.
*G06T 19/20* (2011.01)
*G06T 5/50* (2006.01)
(Continued)

(52) U.S. Cl.
CPC ................ *G06T 19/20* (2013.01); *G06T 5/50* (2013.01); *G06T 13/40* (2013.01); *G06V 10/44* (2022.01);
(Continued)

(58) Field of Classification Search
None
See application file for complete search history.

(56) References Cited

U.S. PATENT DOCUMENTS

| 2009/0146378 | A1* | 6/2009 | Van Luchene | ...... A63F 3/00157 273/431 |
| 2014/0285517 | A1* | 9/2014 | Park | ........................ G06T 13/40 345/632 |
| 2015/0227652 | A1* | 8/2015 | Aonuma | ................ G06V 40/23 703/11 |

FOREIGN PATENT DOCUMENTS

| CN | 109151430 A * | 1/2019 |
| EP | 2784751 A2 | 10/2014 |

(Continued)

OTHER PUBLICATIONS

"Create your own original caricature character!", Nintendo, WiiSports, URL: https://web.archive.org/web/20061206182618/http://www.nintendo.co.jp/wii/rspj/mii/index.html, Dec. 6, 2006, 03 pages.
(Continued)

*Primary Examiner* — Steven Z Elbinger
(74) *Attorney, Agent, or Firm* — CHIP LAW GROUP

(57) ABSTRACT

Provided is an information processing apparatus and an information processing method capable of providing more effective learning content in learning motion of a body. An
(Continued)

adjustment unit generates an adjusted second virtual object by adjusting, on the basis of feature point information of a first person included in a first virtual object reflecting a body motion of the first person, a second virtual object reflecting a body motion of a second person to be superimposed on the first virtual object. The technology according to the present disclosure can be applied to, for example, an information processing apparatus such as a smartphone.

18 Claims, 33 Drawing Sheets

(51) Int. Cl.
  *G06T 13/40* (2011.01)
  *G06V 10/44* (2022.01)
  *G06V 10/74* (2022.01)
  *G06V 40/20* (2022.01)
(52) U.S. Cl.
  CPC ............ *G06V 10/761* (2022.01); *G06V 40/23* (2022.01); *G06T 2207/20044* (2013.01); *G06T 2207/20221* (2013.01); *G06T 2219/2004* (2013.01)

(56) References Cited

FOREIGN PATENT DOCUMENTS

| | | |
|---|---|---|
| JP | 2013-167941 A | 8/2013 |
| JP | 2015-146980 A | 8/2015 |

OTHER PUBLICATIONS

"Baseball", Nintendo, WiiSports, URL: https://web.archive.org/web/20061205103216/http://www.nintendo.co.jp/wii/rspj/5sports/baseball.html, Dec. 5, 2006, 03 pages.

"Boxing", Nintendo, WiiSports, URL: https://web.archive.org/web/20110925152014/http://www.nintendo.co.jp/wii/rspj/5sports/boxing.html, Sep. 25, 2011, 03 pages.

International Search Report and Written Opinion of PCT Application No. PCT/JP2021/017146, issued on Jul. 27, 2021, 10 pages of ISRWO.

* cited by examiner

FIG. 4

| | UC1 | UC2 | UC3 | UC4 | UC5 |
|---|---|---|---|---|---|
| APPLIED DIGITAL TWIN | TEACHER: REAL TIME<br>STUDENT: REAL TIME | TEACHER: REAL TIME<br>VIDEO CONTENT<br>STUDENT: REAL TIME | TEACHER: REAL TIME<br>STUDENT: VIDEO CONTENT | TEACHER: REAL TIME<br>VIDEO CONTENT<br>STUDENT: VIDEO CONTENT | TEACHER: VIDEO CONTENT<br>STUDENT: VIDEO CONTENT |
| USE CASE | REAL-TIME STUDIO CLASS | REAL-TIME STUDIO CLASS<br><br>(PROCEED BY SWITCHING BETWEEN CASE WHERE TEACHER PERFORMS IN REAL TIME AND CASE WHERE TEACHER SHOWS VIDEO CONTENT) | REAL-TIME STUDIO CLASS<br><br>(TEACHER ADDS INSTRUCTION INFORMATION FOR VIDEO CONTENT OF STUDENT IN REAL TIME) | REAL-TIME STUDIO CLASS<br><br>(PROCEED BY SWITCHING BETWEEN CASE WHERE TEACHER ADDS INSTRUCTION INFORMATION FOR VIDEO CONTENT OF STUDENT IN REAL TIME AND CASE WHERE TEACHER SHOWS VIDEO CONTENT) | SELF-CONDITIONING OF GOLF<br><br>(CONFIRM MOTION BY STUDENT ONESELF BY SUPERIMPOSING CURRENT VIDEO CONTENT OF STUDENT ON OWN PAST VIDEO CONTENT AS MODEL) |
| SYSTEM CONFIGURATION | DEVICE + MEC | DEVICE + MEC + CLOUD | DEVICE + MEC + CLOUD | DEVICE + MEC + CLOUD | DEVICE + MEC + CLOUD |

INFORMATION PROCESSING APPARATUS AND INFORMATION PROCESSING METHOD FOR ALIGNING A SECOND VIRTUAL OBJECT WITH A FIRST VIRTUAL OBJECT

CROSS REFERENCE TO RELATED APPLICATIONS

This application is a U.S. National Phase of International Patent Application No. PCT/JP2021/017146 filed on Apr. 30, 2021, which claims priority benefit of Japanese Patent Application No. JP 2020-084483 filed in the Japan Patent Office on May 13, 2020. Each of the above-referenced applications is hereby incorporated herein by reference in its entirety.

TECHNICAL FIELD

The present disclosure relates to an information processing apparatus, an information processing method, and a program, and more particularly, to an information processing apparatus, an information processing method, and a program capable of providing more effective learning content in learning motion of a body.

BACKGROUND ART

Conventionally, there is a technology in which a video image captured a state of an instructor performing exercise such as aerobics, yoga, or dance and a video image captured a state of a user performing exercise are displayed side by side, so that the user can easily learn the exercise of the instructor.

Furthermore, in recent years, athletes exercise wearing devices capable of receiving various types of information externally via a network. For example, Patent Literature 1 discloses a technique in which, at a place where one athlete is exercising, virtual objects of other athletes who have exercised in the past at the place are superimposed and displayed on a display unit showing the surroundings.

CITATION LIST

Patent Document

Patent Document 1: Japanese Patent Application Laid-Open No. 2013-167941

SUMMARY OF THE INVENTION

Problems to be Solved by the Invention

By the way, if the video in which the instructor is exercising and the video in which the user is exercising can be displayed in a superimposed manner, the user can learn the movement of the instructor more accurately.

The present disclosure has been made in view of such a situation, and an object of the present disclosure is to provide more effective learning content in learning movement of a body.

Solutions to Problems

An information processing apparatus according to the present disclosure includes an adjustment unit configured to generate an adjusted second virtual object by adjusting, on the basis of feature point information of a first person included in a first virtual object reflecting a body motion of the first person, a second virtual object reflecting a body motion of a second person to be superimposed on the first virtual object.

An information processing method according to the present disclosure is an information processing method including: by an information processing apparatus, generating an adjusted second virtual object by adjusting, on the basis of feature point information of a first person included in a first virtual object reflecting a body motion of the first person, a second virtual object reflecting a body motion of a second person to be superimposed on the first virtual object.

A program according to the present disclosure is a program causing a computer to execute processing of generating an adjusted second virtual object by adjusting, on the basis of feature point information of a first person included in a first virtual object reflecting a body motion of the first person, a second virtual object reflecting a body motion of a second person to be superimposed on the first virtual object.

According to the present disclosure, an adjusted second virtual object is generated by adjusting, on the basis of feature point information of a first person included in a first virtual object reflecting a body motion of the first person, a second virtual object reflecting a body motion of a second person to be superimposed on the first virtual object.

BRIEF DESCRIPTION OF DRAWINGS

FIG. 4 is a diagram for describing a use case to which a digital twin is applicable.

MODE FOR CARRYING OUT THE INVENTION

Embodiments for carrying out the present disclosure (hereinafter referred to as an embodiment) are now described. Moreover, the description is given in the following order.

1. Overview of technology according to present disclosure and use case
2. Configuration and operation of information processing system
3. Application example of 5G network slicing
4. Modifications
5. Configuration example of computer 1. Overview of Technology According to Present Disclosure and Use Case (Overview of Information Processing System)

Figure 1:
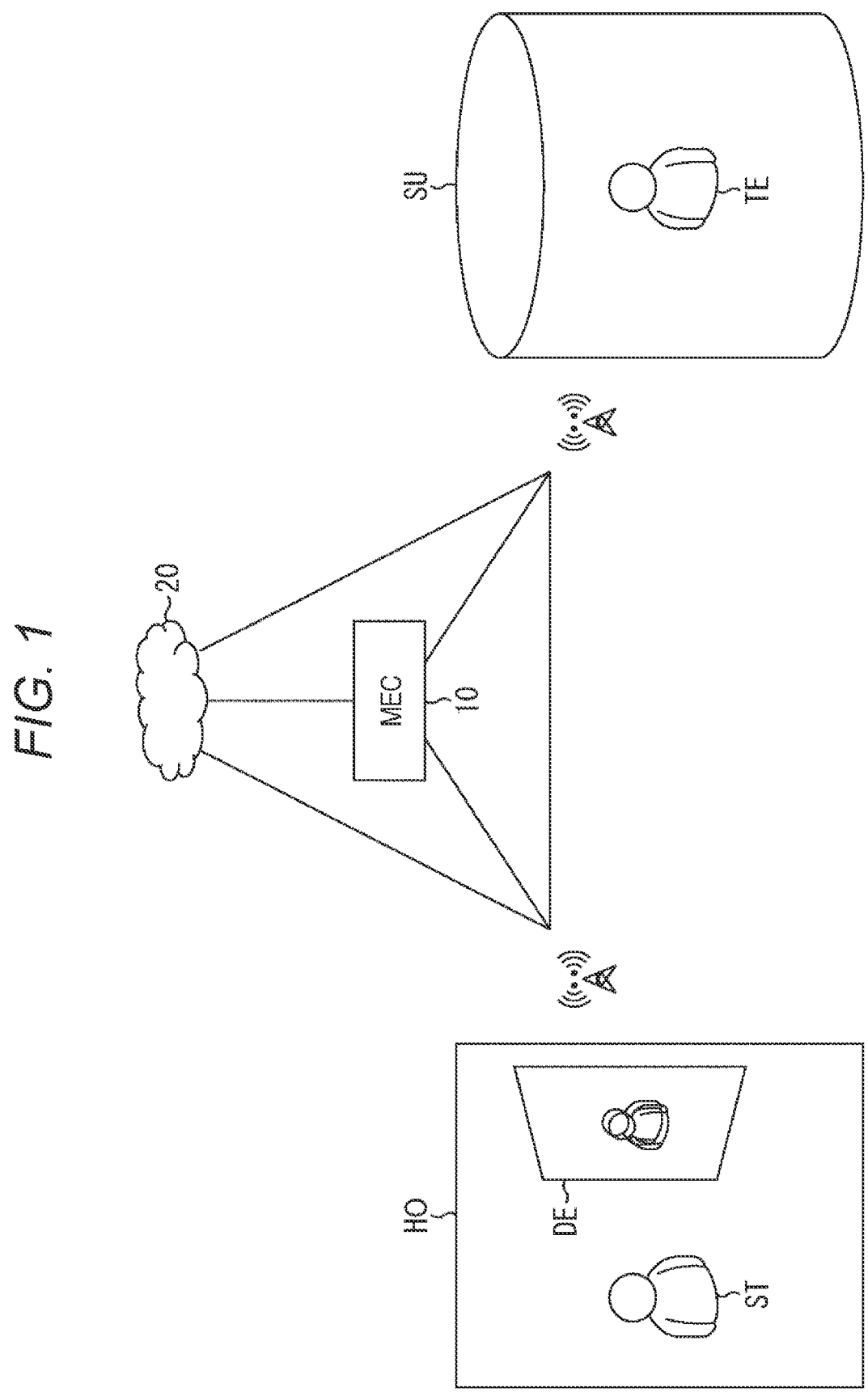
FIG. 1 is a diagram illustrating an example of an outline of an information processing system to which a technology according to the present disclosure is applied.

FIG. 1 is a diagram illustrating an example of an outline of an information processing system to which a technology according to the present disclosure is applied.

In the information processing system of FIG. 1, a reference digital twin, which is a virtual object reflecting the body motion, such as aerobics, yoga, and dance, of an instructor TE who is a reference person in a studio SU, is superimposed on a user digital twin, which is a virtual object reflecting the body motion of a user ST in a home HO, and is displayed on a device DE in the home HO.

In general, the digital twin refers to an object or an environment in a real space, information indicating a state of the object or the environment, or the like constructed and represented in real time in a virtual space, or a technology therefor. The digital twin in the present embodiment refers to a virtual object in which a skeleton, a body shape, and movement of a person in a real space are reflected in real time on a virtual space. Specifically, the digital twin is three-dimensionally modeled computer graphics (3DCG) of three-dimensional information of a person displayed on a virtual space. The digital twin is generated on the basis of sensor data acquired by sensing the instructor TE and the user ST by one or a plurality of sensors installed in the studio SU or the home HO. The digital twin may be drawn with the skeleton, body shape, and scale of the corresponding person as they are, or may be drawn with the skeleton, body shape, and scale adjusted for the purpose of protecting the privacy of the person.

Hereinafter, the reference digital twin of the instructor TE is referred to as a teacher digital twin, and the user digital twin of the user ST is referred to as a student digital twin as appropriate.

The user ST can learn the movement of the instructor TE more accurately by moving own body while watching the movement of the teacher digital twin superimposed on the student digital twin.

Furthermore, the instructor TE can give an instruction regarding the movement of the user ST to the user ST by viewing the movement of the student digital twin superimposed on the teacher digital twin in the studio SU.

The studio SU and the home HO may directly exchange (transmit and receive) information by wired communication or wireless communication, or may exchange (transmit and receive) information via a mobile edge computing (MEC) server 10 or a cloud server 20. In a case where transmission and reception of information are performed by wireless communication, a communication system such as long term evolution (LTE), Wi-Fi (registered trademark), 4G, or 5G can be applied to a part or the whole of the wireless communication.

(Example of Superimposed Video)

An example of a superimposed video in which the teacher digital twin is superimposed on the student digital twin displayed on the device DE in the home HO will be described with reference to FIGS. 2 and 3.

Figure 2:
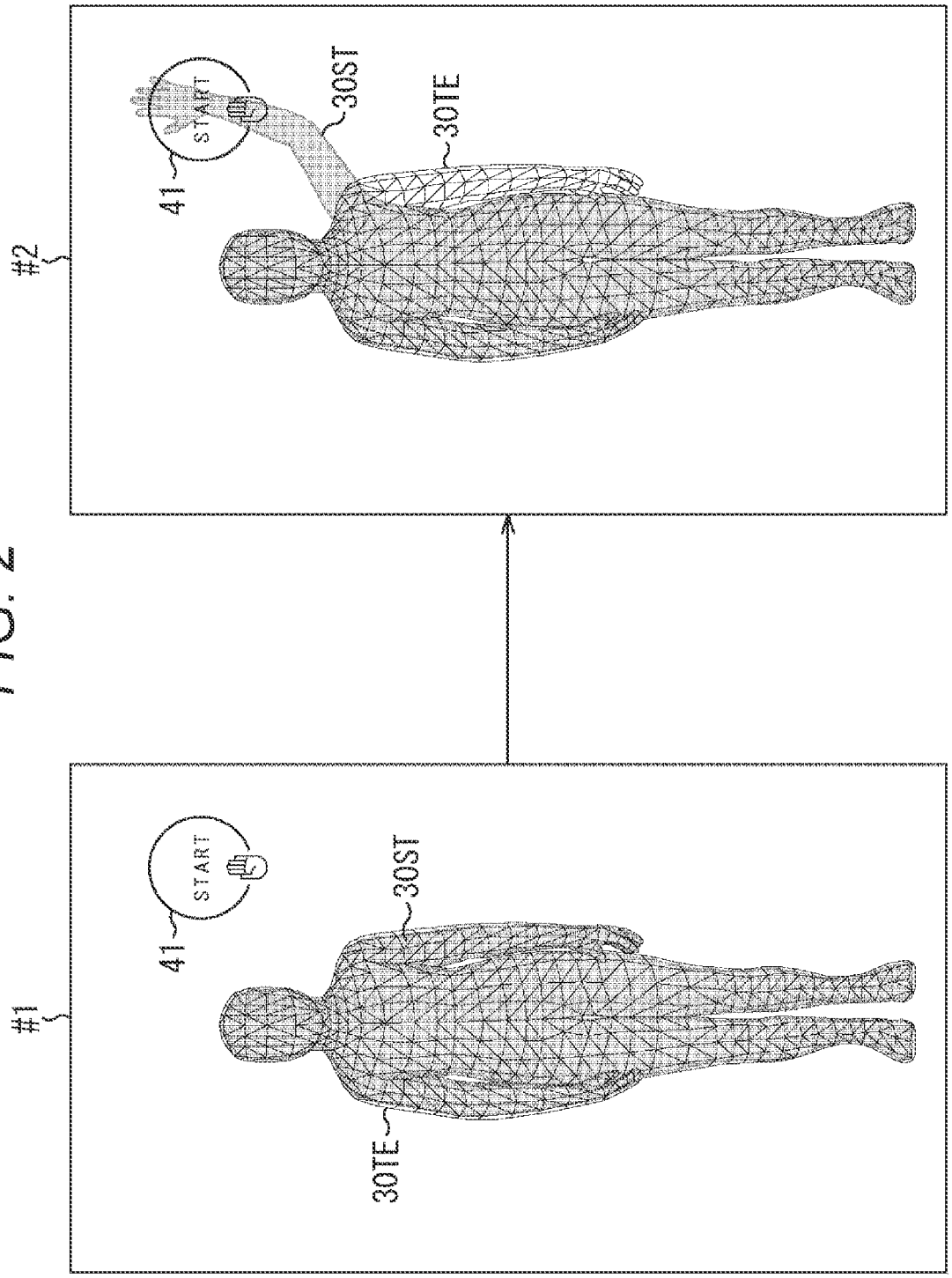
FIG. 2 is a diagram illustrating an example of a superimposed video.

In the state of the screen #1 of FIG. 2, on a student digital twin 30ST that is upright, a lattice-shaped teacher digital twin 30TE, which is also upright, is superimposed. In the drawing, a button 41, which is a graphical user interface (GUI) for starting a lesson by the instructor TE in the studio SU, is displayed on the upper right of the screen #1.

As illustrated in the state of the screen #2, if the user ST raises one hand and it is determined that the hand of the corresponding student digital twin 30ST overlaps the area of the button 41, the lesson by the instructor TE is started. Here, determination processing based on the positional relationship between the coordinates of the button 41 in the virtual space and the coordinates of the hand of the student digital twin 30ST is performed. Therefore, even if the hand of the student digital twin 30ST overlaps the area of the button 41 in front view as in the screen #2, the lesson is not started in a case where the hand of the student digital twin 30ST is deviated from the area of the button 41 in the depth direction.

Figure 3:
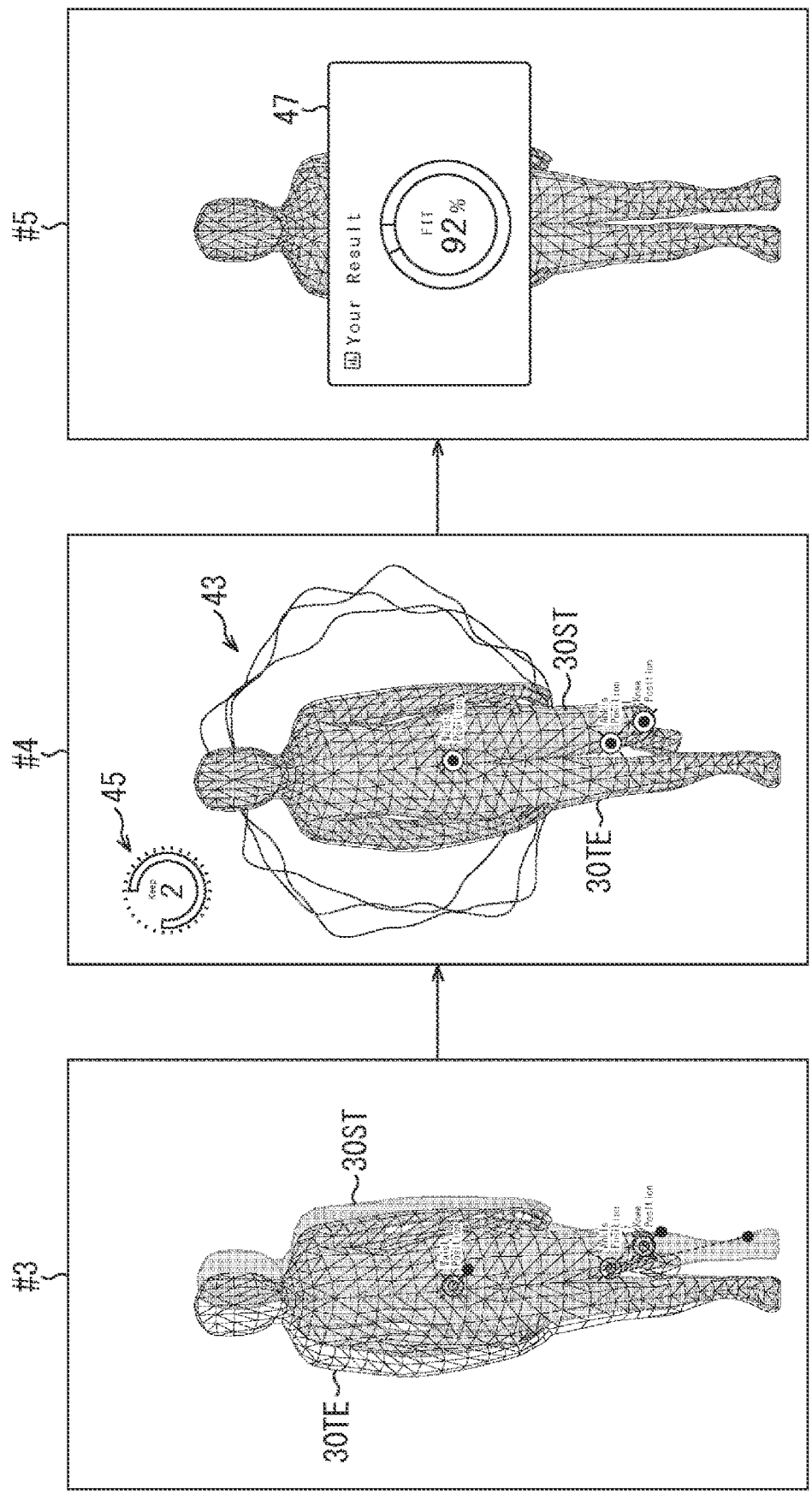
FIG. 3 is a diagram illustrating an example of a superimposed video.

In the state of the screen #3 of FIG. 3, the teacher digital twin 30TE in which the instructor TE bends one knee from the upright state and stands on one leg so as to bend the corresponding knee and stand on one leg is displayed. Furthermore, an attention point (fitting point) indicating a body part to be moved in the exercise is superimposed and displayed on the teacher digital twin 30TE and the student digital twin 30ST. Specifically, the fitting points indicating the positions of the waist, the knee, and the heel in the state of standing on one leg of the teacher digital twin 30TE and the fitting points indicating the positions of the waist, the knee, and the heel in the upright state (before standing on one leg) of the student digital twin 30ST are displayed.

In this way, the movement of the user ST can be guided by displaying the fitting points of the teacher digital twin 30TE and the student digital twin 30ST. Note that, in addition to the fitting points, lines and figures that assist and guide the movement of the user ST may be superimposed and displayed on the teacher digital twin 30TE and the student digital twin 30ST.

In the state of the screen #4, the user ST stands on one leg in accordance with the movement of the teacher digital twin 30TE, so that the fitting points of the student digital twin 30ST match the fitting points of the teacher digital twin 30TE. At this time, an effect video 43 that recommends to maintain the posture is displayed around (in the background of) the student digital twin 30ST. Furthermore, an indicator 45 indicating the time during which the user ST (student digital twin 30ST) maintains the posture is displayed on the upper left of the screen #4.

On the screens #3 and #4, superimposed videos in a front view (the student digital twin 30ST and the teacher digital twin 30TE) are displayed, but superimposed videos at different viewpoints (angles) can also be displayed. As a result, the user ST can confirm the deviation from the movement of the instructor TE in more detail.

Furthermore, an effect video may be superimposed on a part (portion) where there is a difference in movement between the student digital twin 30ST and the teacher digital twin 30TE such that the part is highlighted. Further, on the contrary, an effect video may be superimposed on a part (portion) where movements are matched between the student digital twin 30ST and the teacher digital twin 30TE such that the part is highlighted.

When the exercise as shown in the screens #3 and #4 is repeated and the lesson ends, a pop-up 47 showing the result of the lesson is displayed as shown in the state of the screen #5. In the pop-up 47, a matching rate of the motion is illustrated as the evaluation result of the exercise of the student digital twin 30ST with respect to the teacher digital twin 30TE. The evaluation result of the exercise is not limited to the matching rate, and the degree of achievement according to the level of the exercise or the like may be scored and indicated.

In this manner, the user ST can learn the exercise of the instructor TE and recognizes the degree of achievement of the user's own exercise while watching the superimposed video.

(Applicable Use Case)

Here, a use case to which the digital twin as described above can be applied will be described with reference to FIG. 4. FIG. 4 illustrates five use cases UC1 to UC5.

In the use case UC1, a digital twin reflecting the teacher's body motion in real time is applied as the teacher digital twin. Further, a digital twin reflecting the student's body motion in real time is applied as the student digital twin.

The use case UC1 can be applied to, for example, a case in which an instructor who is a teacher handles classes such as aerobics, yoga, and dance in real time from a studio to a student who is a user at home (real-time studio class). Note that, in this use case, the teacher can handle a real-time class not only from the studio but also from home or any other space, and the same applies to the subsequent use cases. The use case UC1 can be implemented by a system configuration including devices on a teacher side and a student side and the MEC server 10.

In the use case UC2, as the teacher digital twin, a digital twin in which the teacher's body motion is reflected in real time or a digital twin in which the teacher's body motion reflected in video content captured in advance (recoded content) is reflected is applied. Further, a digital twin reflecting the student's body motion in real time is applied as the student digital twin.

Similarly to the use case UC1, the use case UC2 can be applied to a real-time class such as aerobics, yoga, and dance. However, in the real-time class of the use case UC2, the teacher can proceed by switching between a case where the teacher performs in real time and a case where the teacher shows the video content (presents a digital twin based on the video content). Furthermore, the use case UC2 can also be applied to, for example, a soccer school in which a professional soccer player teaches a junior-level player how to shoot (kick) or dribble. The use case UC2 can be implemented by a system configuration including devices on a teacher side and a student side, the MEC server 10, and the cloud server 20 capable of handling video content.

In the use case UC3, a digital twin reflecting the teacher's body motion in real time is applied as the teacher digital twin. Furthermore, as the student digital twin, a digital twin reflecting the body motion of the student appeared in the video content captured in advance is applied.

Similarly to the use case UC1, the use case UC3 can also be applied to a real-time class such as aerobics, yoga, and dance. However, in the real-time class of the use case UC3, the teacher confirms the movement of the student digital twin based on the video content of the student, so that instruction information such as an instruction and advice for the video content of the student can be added in real time. The use case UC3 can also be applied to, for example, a soccer school in which a professional soccer player teaches a junior-level player how to shoot or dribble. The use case UC3 can be implemented by a system configuration including devices on the teacher side and the student side, the MEC server 10, and the cloud server 20 capable of handling video content.

In the use case UC4, as the teacher digital twin, a digital twin in which the teacher's body motion is reflected in real time or a digital twin in which the teacher's body motion reflected in video content captured in advance is reflected is applied. Furthermore, as the student digital twin, a digital twin reflecting the body motion of the student appeared in the video content captured in advance is applied.

Similarly to the use case UC1, the use case UC4 can also be applied to a real-time class such as aerobics, yoga, and dance. However, in the real-time class of the use case UC3, the teacher can proceed by switching a case where instruction information such as an instruction or advice for the video content of the student is added and a case where the video content is shown in real time. The use case UC4 can also be applied to, for example, a soccer school in which a professional soccer player teaches a junior-level player how to shoot or dribble. The use case UC4 can be implemented by a system configuration including devices on the teacher side and the student side, the MEC server 10, and the cloud server 20 capable of handling video content.

In the use case UC5, as both the teacher digital twin and the student digital twin, a digital twin reflecting the body motion of the student appeared in the video content captured in advance is applied.

The use case UC5 can be applied to, for example, self-conditioning of golf (confirmation of an action such as a swing performed by oneself). Specifically, the student can confirm the action by oneself by superimposing the digital twin based on the current video content on the digital twin based on own past video content as a model (treating the digital twin based on the past video content as the teacher digital twin). The use case UC5 can also be applied to, for example, self-conditioning of shooting and dribbling for a professional soccer player. The use case UC5 can be implemented by a system configuration including devices on the student side, the MEC server 10, and the cloud server 20 capable of handling video content.

2. Configuration and Operation of Information Processing System

Hereinafter, a specific configuration and operation of an information processing system to which the technology according to the present disclosure is applied will be described.

(Configuration Example of Information Processing System)

Figure 5:
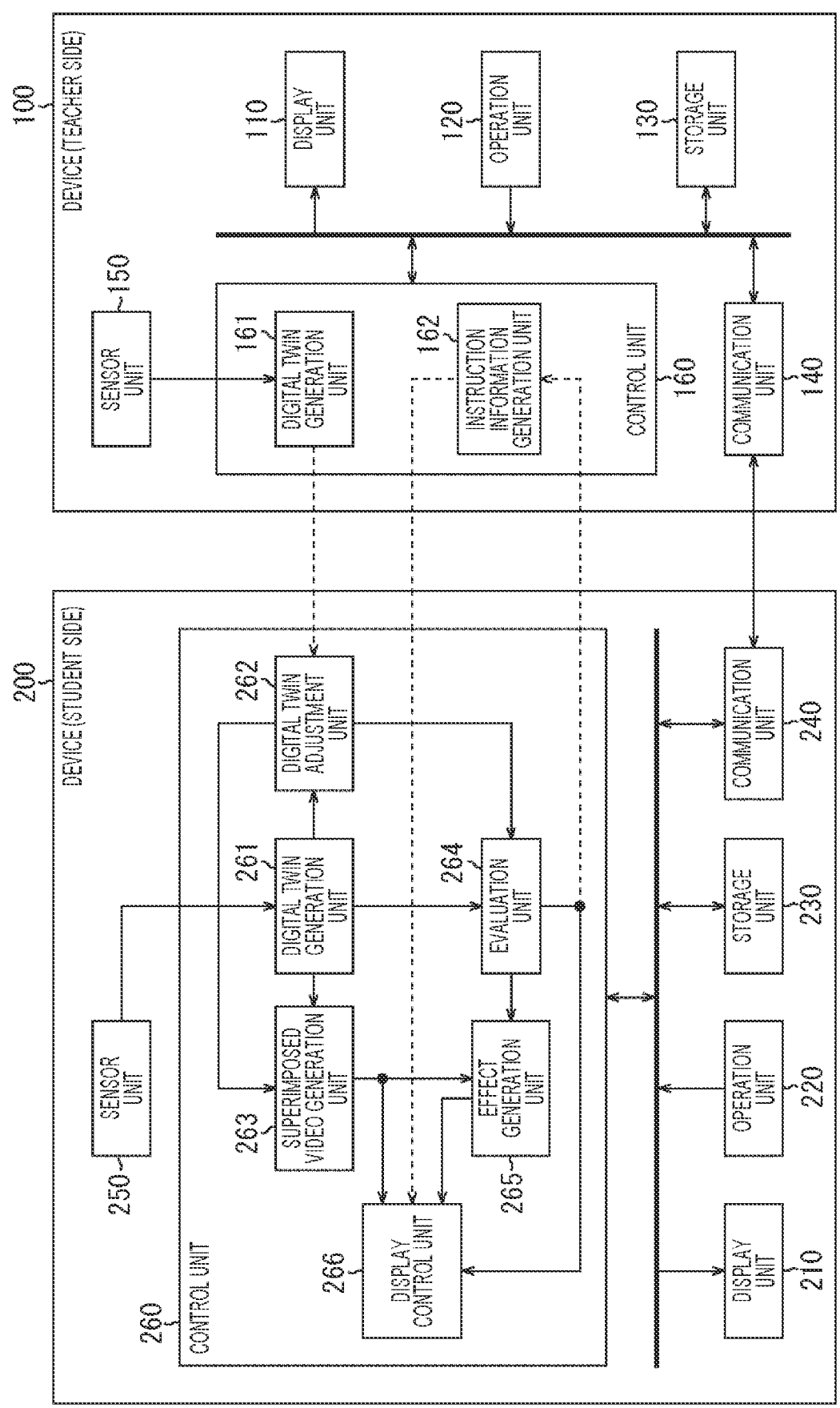
FIG. 5 is a block diagram illustrating a functional configuration example of an information processing system.

FIG. 5 is a block diagram illustrating a configuration example of an information processing system to which the technology according to the present disclosure is applied.

The information processing system in FIG. 5 includes a device 100 on the teacher side and a device 200 on the student side. In the example of FIG. 5, the device 100 on the teacher side and the device 200 on the student side are configured to directly communicate with each other, but may also communicate via the MEC server 10 or the cloud server 20.

The device 100 on the teacher side is installed in a space such as a studio or a house where a teacher (an instructor or the like) is located.

On the other hand, the device 200 on the student side is installed in a space such as a studio or a house where a student (user) is located.

In a case where the device 100 on the teacher side and the device 200 on the student side are installed in a wide space such as a studio, for example, they are configured as a relatively large device (or system) such as a device having a booth type housing surrounding the periphery of a person or a device having a whole-body mirror type display surface in which the entire body of the person is reflected. On the other hand, in a case where the device 100 on the teacher side and the device 200 on the student side are installed in a narrow space such as a home, for example, they are configured as a small-scale device (or system) such as a smartphone including various sensors or a display connectable to the smartphone. Note that the device 100 on the teacher side and the device 200 on the student side may be configured as devices (or systems) of the same scale.

The device 100 on the teacher side includes a display unit 110, an operation unit 120, a storage unit 130, a communication unit 140, a sensor unit 150, and a control unit 160.

The display unit 110 includes a liquid crystal display, an organic electro-luminescence (EL) display, or the like, and displays the digital twin and various types of information on the basis of the control of the control unit 160.

The operation unit 120 includes a touch panel integrated with a display constituting the display unit 110, a physical button provided on a housing of the device 100, a microphone, and the like. The operation unit 120 receives an operation by the teacher and supplies operation information corresponding to the operation to the control unit 160.

The storage unit 130 stores programs necessary for operating the device 100, various data set in advance by the teacher and desired to be used in the lesson, and the like.

The communication unit 140 includes a network interface and the like, and communicates with the device 200 on the student side on the basis of the control of the control unit 160.

The sensor unit 150 includes one or a plurality of sensors, and supplies various sensor data acquired by sensing the body motion of the teacher to the control unit 160.

For example, the sensor unit 150 includes one or a plurality of time of flight (ToF) sensors and an RGB sensors. The control unit 160 generates the teacher digital twin on the basis of the ToF data acquired by the ToF sensor and the RGB data (video data) acquired by the RGB sensor. In a case where the sensor unit 150 includes a plurality of ToF sensors and RGB sensors, the control unit 160 can also generate the teacher digital twin on the basis of the volumetric capture data generated by the volumetric capture using the acquired sensor data. The sensor unit 150 may include various sensors capable of acquiring sensor data other than ToF data and RGB data.

The control unit 160 executes various processing on the basis of a program stored in the storage unit 130, operation information from the operation unit 120, and information acquired via the communication unit 140.

The control unit 160 includes a digital twin generation unit 161 and an instruction information generation unit 162. Each functional unit included in the control unit 160 is implemented by executing a program stored in the storage unit 130.

Meanwhile, the device 200 on the student side includes a display unit 210, an operation unit 220, a storage unit 230, a communication unit 240, a sensor unit 250, and a control unit 260.

The display unit 210 includes a liquid crystal display, an organic EL display, or the like, and displays the digital twin and various types of information on the basis of the control of the control unit 260.

The operation unit 220 includes a touch panel integrated with a display constituting the display unit 210, a physical button provided on a housing of the device 200, a microphone, and the like. The operation unit 220 receives an operation by the student and supplies operation information corresponding to the operation to the control unit 260.

The storage unit 230 stores programs necessary for operating the device 200, various data prepared in advance by the student, and the like.

The communication unit 240 includes a network interface and the like, and communicates with the device 100 on the teacher side on the basis of the control of the control unit 260.

The sensor unit 250 includes a plurality of sensors, and supplies various sensor data acquired by sensing the body motion of the student to the control unit 260.

Specifically, the sensor unit 250 includes one or a plurality of ToF sensors and an RGB sensors. The sensor unit 250 of the device 200 on the student side may be configured similarly to the sensor included in the device 100 on the teacher side, or may be calibrated from a sensor with a different number or type from the sensor included in the device 100 on the teacher side.

The control unit 260 executes various processing on the basis of a program stored in the storage unit 230, operation information from the operation unit 220, and information acquired via the communication unit 240.

The control unit 260 includes a digital twin generation unit 261, a digital twin adjustment unit 262, a superimposed video generation unit 263, an evaluation unit 264, an effect generation unit 265, and a display control unit 266. Each functional unit included in the control unit 260 is implemented by executing a program stored in the storage unit 230.

As illustrated in FIG. 5, each functional unit included in the control unit 160 of the device 100 on the teacher side and each functional unit included in the control unit 260 of the device 200 on the student side execute each processing by transmitting and receiving information to and from each other as indicated by arrows in the figure. In FIG. 5, the information corresponding to the dashed arrows is actually transmitted and received via the communication unit 140 of the device 100 on the teacher side and the communication unit 240 of the device 200 on the student side.

Hereinafter, details of each functional unit included in the device 100 (the control unit 160) on the teacher side and each functional unit included in the device 200 (the control unit 260) on the student side will be described.

(Details of Digital Twin Generation Unit)

Figure 6:
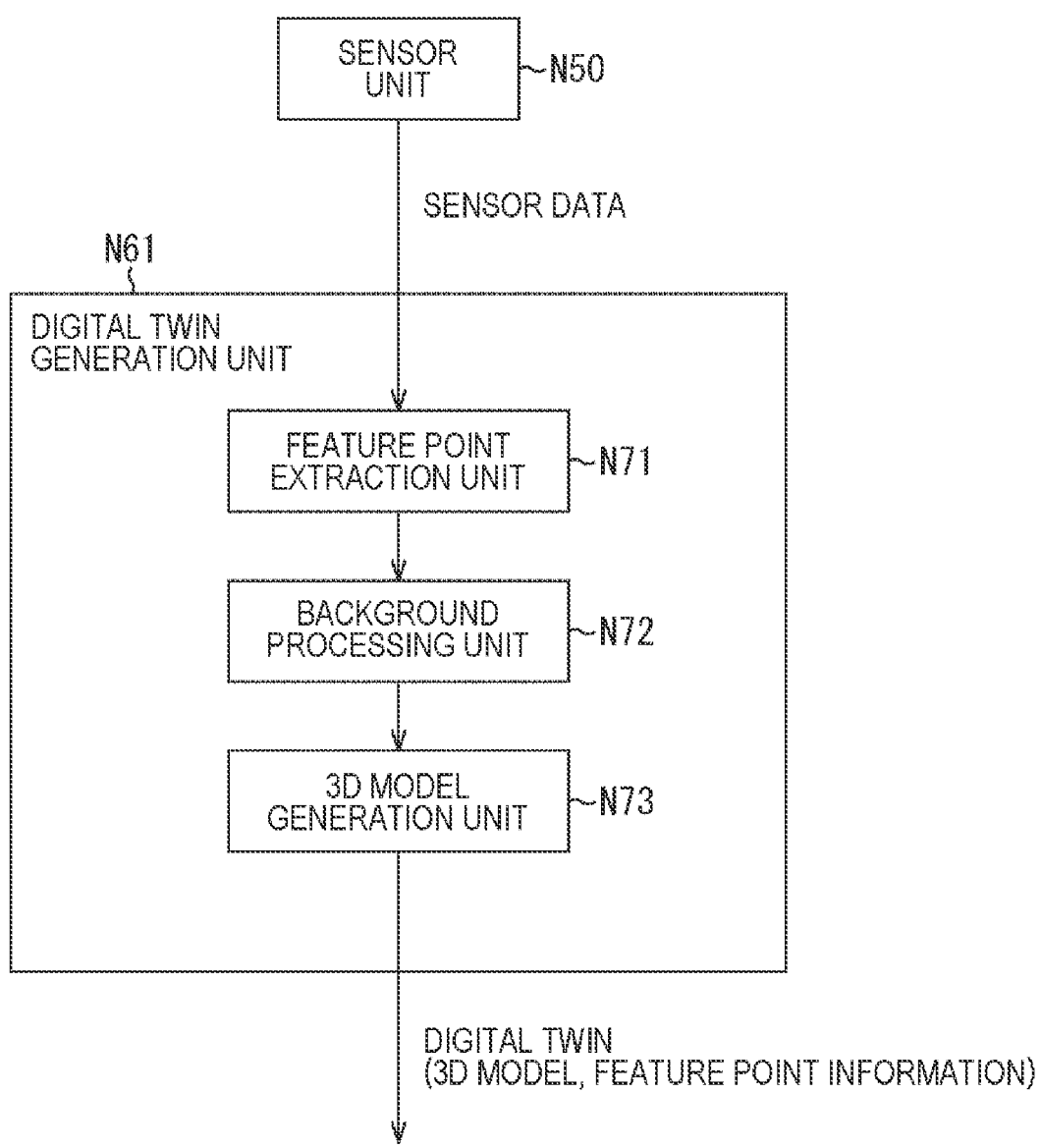
FIG. 6 is a diagram for explaining details of a digital twin generation unit.

FIG. 6 is a diagram for explaining details of the digital twin generation unit 161 of the device 100 on the teacher side and the digital twin generation unit 261 of the device 200 on the student side.

Note that the digital twin generation unit 161 of the device 100 on the teacher side and the digital twin generation unit 261 of the device 200 on the student side are configured in a similar manner, and thus will be described as a digital twin generation unit N61 as illustrated in FIG. 6. Furthermore, the sensor unit 150 of the device 100 on the teacher side and the sensor unit 250 of the device 200 on the student side will be similarly described as the sensor unit N50.

The digital twin generation unit N61 generates, on the basis of a body motion of a person, a virtual object that performs a body motion similar to that of the person, that is, a digital twin reflecting the body motion of the person. The digital twin generation unit N61 includes a feature point extraction unit N71, a background processing unit N72, and a 3D model generation unit N73.

On the basis of the sensor data from the sensor unit N50, the feature point extraction unit N71 extracts, as feature point information of the person, skeleton information indicating a skeleton and joint points of the person (teacher or student), three-dimensional contour information indicating a three-dimensional contour of the person, and acceleration information indicating a motion of a body of the person. The feature point information is set as data on a time axis that continuously changes with time.

The skeleton information is extracted, for example, by performing skeleton estimation using machine learning or the like. The skeleton estimation may be performed using only one of the ToF data and the RGB data, or may be performed using both the ToF data and the RGB data.

The three-dimensional contour information is extracted on the basis of, for example, a depth image including ToF data.

The acceleration information is calculated on the basis of, for example, displacements of the skeleton and the joint points indicated by the skeleton information. In a case where the person wears an acceleration sensor as one of the sensor units N50 on each part of the body, the acceleration information may be acquired on the basis of the sensor data from the acceleration sensor. The acceleration information also includes left and right information indicating which any of the body parts (hands, arms, legs, etc.) on the left and right side is moving.

These pieces of feature point information are supplied to the background processing unit N72 together with RGB data (video data).

The background processing unit N72 removes the background of the person in the video data on the basis of the feature point information from the feature point extracting unit N71 and the video data. The video data from which the background has been removed is supplied to the 3D model generation unit N73 together with the feature point information.

The 3D model generation unit N73 generates a digital twin of the person on the basis of the video data from which the background has been removed and the feature point information from the background processing unit N72.

First, the 3D model generation unit N73 models a target person on the basis of the three-dimensional contour information to create a three-dimensional model (3D model). Next, the 3D model generation unit N73 associates the skeleton and the joint points indicated by the skeleton information with the created 3D model. As a result, the body motion of the person can be reflected in the 3D model. Then, the 3D model generation unit N73 synthesizes skin data corresponding to human skin with the 3D model.

As the skin data, skin data having different visual texture is prepared for each purpose of body motion of the person. The purpose of the body motion includes, for example, aerobics, yoga, dance, golf, soccer, and the like, and is selected in advance by a teacher or a student. In addition, the purpose of the body motion is not limited to the sports described above, and may include artistic creation activities such as playing a musical instrument such as a guitar or a piano, and operating a potter's wheel in porcelain.

Then, the 3D model generation unit N73 synthesizes skin data corresponding to the selected purpose of the body motion with respect to the 3D model, thereby generating a digital twin of a type corresponding to the purpose. For example, in a case where soccer is selected as the purpose of the body motion, the digital twin for soccer is generated by synthesizing the skin data for soccer with respect to the 3D model. At this time, for the generated digital twin, meta-information indicating the purpose of the body motion (for example, soccer) may be stored in association with the sensor data.

As described above, the digital twin generation unit N61 extracts the feature point information on the basis of the sensor data, and generates a digital twin as a 3D model on the basis of the extracted feature point information. The feature point information extracted on the basis of the sensor data is added to the generated digital twin and output to the subsequent stage.

(Details of Instruction Information Generation Unit)

Figure 7:
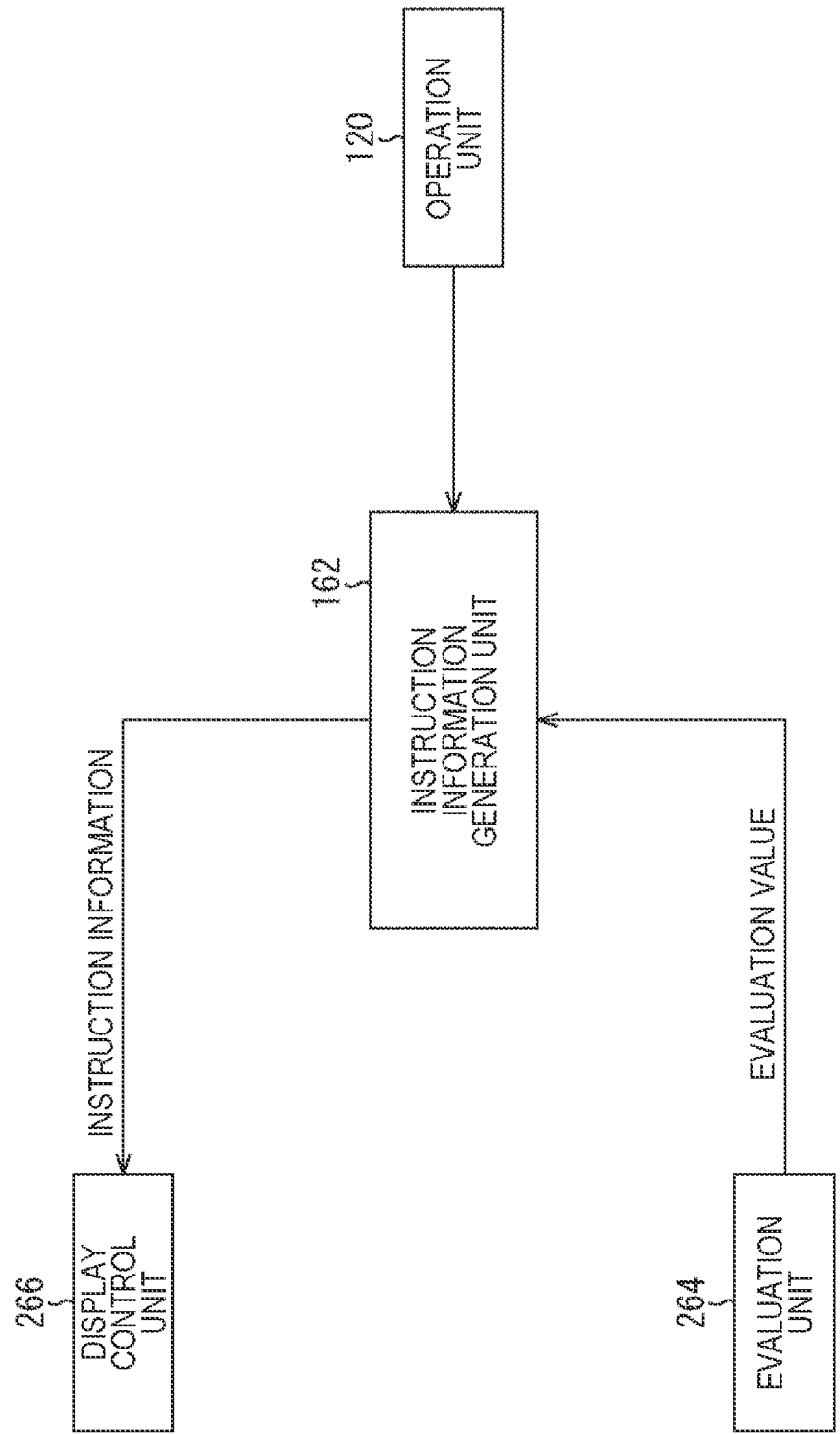
FIG. 7 is a diagram for explaining details of an instruction information generation unit.

FIG. 7 is a diagram illustrating details of the instruction information generation unit 162 of the device 100 on the teacher side.

The instruction information generation unit 162 generates instruction information indicating an instruction or the like for the student on the basis of the operation information corresponding to the operation of the operation unit 120 by the teacher and supplies the instruction information to the display control unit 266 of the device 200 on the student side.

The operation information here includes, for example, setting information for setting a GUI such as the button 41 illustrated in the screens #1 and #2 of FIG. 2, and setting information for setting fitting points illustrated in the screen #3 of FIG. 3. That is, the teacher can set the GUI and the fitting point displayed on the display unit 210 of the device 200 on the student side by operating the operation unit 120.

In this case, the instruction information generation unit 162 generates display information for displaying a GUI or a fitting point as illustrated in FIG. 2 as the instruction information on the basis of the operation information (setting information). Such display information may be generated, for example, on the basis of display data stored in the storage unit 130 or on the basis of display data acquired via the communication unit 140.

Furthermore, the instruction information generation unit 162 may generate the instruction information on the basis of the evaluation value from the evaluation unit 264 of the device 200 on the student side. The evaluation value indicates, for example, an evaluation result (such as a matching rate of motion) of a lesson illustrated in a pop-up 47 on the screen #5 in FIG. 3, and a comment corresponding to the evaluation value is automatically generated as the instruction information. This comment may be prepared in advance for each evaluation value, and a comment corresponding to the evaluation value may be selected. The comment generated as the instruction information may be integrated with the comment input by the teacher as the operation information corresponding to the operation of the operation unit 120. Note that there is a possibility that the teacher cannot input an appropriate comment only with the evaluation result such as the matching rate of the motion. Therefore, the instruction information generation unit 162 may generate the instruction information or receive the input of the comment by the teacher on the basis of the superimposed video or the effect video from the device 200 on the student side or the single student digital twin or the RGB data (video data) of the student.

These pieces of instruction information are displayed on the display unit 210 on the device 200 on the student side under the control of the display control unit 266.

(Details of Digital Twin Adjustment Unit)

Figure 8:
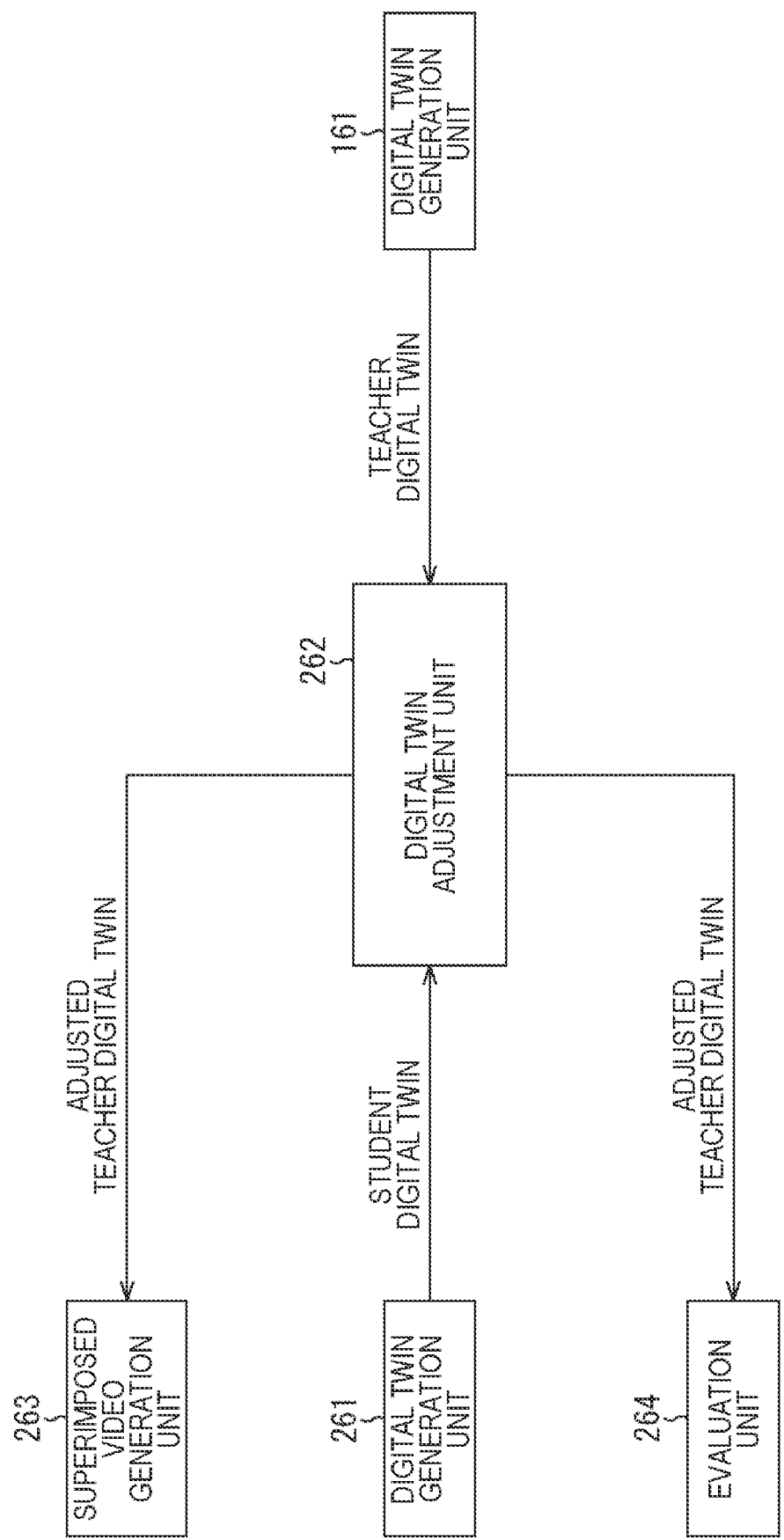
FIG. 8 is a diagram for explaining details of a digital twin adjustment unit.

FIG. 8 is a diagram for explaining details of the digital twin adjustment unit 262 of the device 200 on the student side.

The digital twin adjustment unit 262 generates an adjusted teacher digital twin (adjusted reference digital twin) by adjusting the teacher digital twin from the digital twin generation unit 161 to be superimposed with the student digital twin from the digital twin generation unit 261. The generated adjusted teacher digital twin is supplied to the superimposed video generation unit 263 and the evaluation unit 264.

Here, the teacher digital twin is adjusted on the basis of the student digital twin so that the teacher digital twin is matched to the student digital twin so that the student who is the user can compare the movement of the student and the movement of the teacher who is the instructor and easily copy the teacher's movement.

Specifically, the digital twin adjustment unit 262 changes the feature point information of the teacher included in the teacher digital twin so as to be close to the feature point information of the student on the basis of the feature point information of the student included in the student digital twin.

For example, the size (scale) of the teacher digital twin is adjusted by changing the skeleton information of the teacher digital twin in accordance with the skeleton information of the student digital twin. The left and right information of the teacher digital twin is changed in accordance with the left and right information of the student digital twin, so that the dominant arm and the dominant leg of the teacher digital twin are adjusted. The three-dimensional contour information of the teacher digital twin is changed in accordance with the three-dimensional contour information of the student digital twin, whereby the body shape of the teacher digital twin is adjusted.

Then, the digital twin adjustment unit 262 creates the 3D model on the basis of the changed feature point information of the teacher, thereby generating the adjusted teacher digital twin including the adjusted feature point information as the adjusted 3D model. The digital twin adjustment unit 262 can generate an adjusted teacher digital twin in a similar manner to the digital twin generation unit N61 in FIG. 6.

(Details of Superimposed Video Generation Unit)

Figure 9:
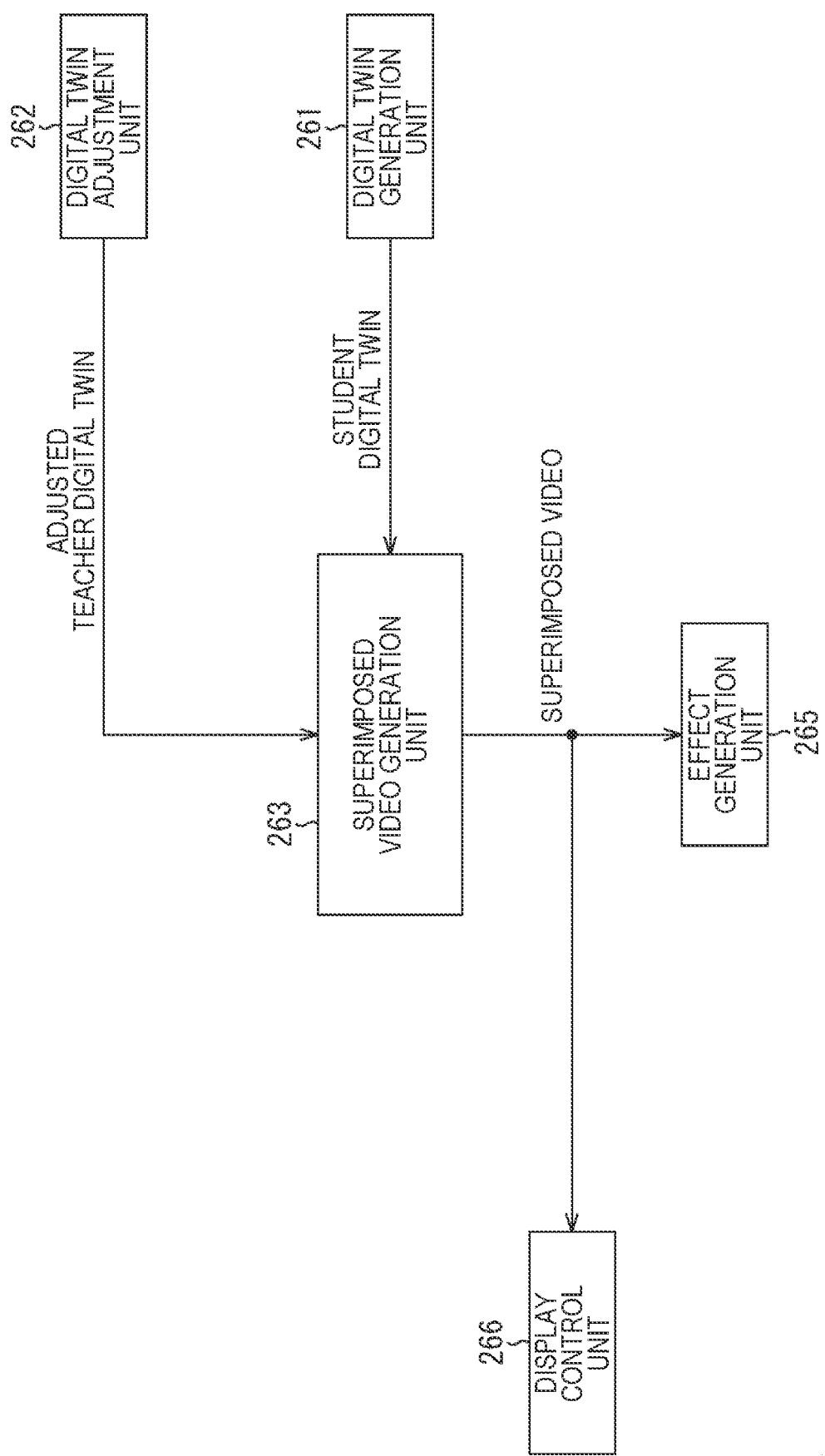
FIG. 9 is a diagram for explaining details of a superimposed video generation unit.

FIG. 9 is a diagram for explaining details of the superimposed video generation unit 263 of the device 200 on the student side.

The superimposed video generation unit 263 generates a superimposed video obtained by superimposing the student digital twin from the digital twin generation unit 261 on the adjusted teacher digital twin from the digital twin adjustment unit 262, and supplies the generated superimposed video to the effect generation unit 265 and the display control unit 266.

Specifically, the superimposed video generation unit 263 maps the adjusted teacher digital twin and the student digital twin to a predetermined reference position on the virtual space, and generates the superimposed video by synchronizing them at a predetermined reference time.

The superimposed video is displayed on the display unit 210 under the control of the display control unit 266.

(Details of Evaluation Unit)

Figure 10:
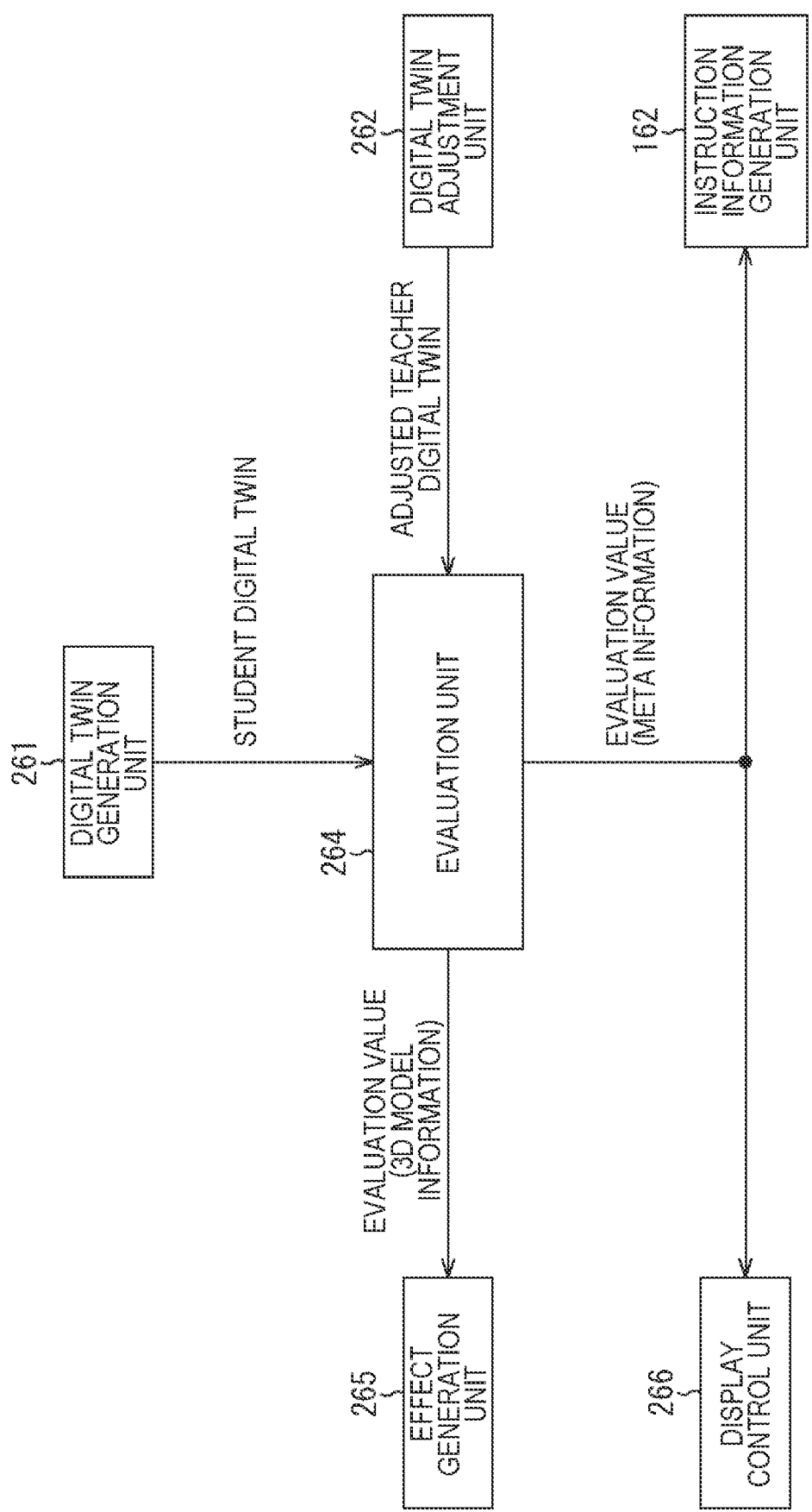
FIG. 10 is a diagram for explaining details of an evaluation unit.

FIG. 10 is a diagram for explaining details of the evaluation unit 264 of the device 200 on the student side.

The evaluation unit 264 calculates an evaluation value of the student digital twin (that is, the body motion of the student) by comparing the student digital twin from the digital twin generation unit 261 with the adjusted teacher digital twin from the digital twin adjustment unit 262.

For example, the evaluation unit 264 obtains a difference in the contour information (deviation in posture) between the student digital twin and the adjusted teacher digital twin as the evaluation value. Further, the evaluation unit 264 obtains a difference in the acceleration information (deviation in movement) between the student digital twin and the adjusted teacher digital twin as the evaluation value. Furthermore, the evaluation unit 264 obtains a difference in the fitting points (deviation in posture) between the student digital twin and the adjusted teacher digital twin as the evaluation value.

Among the evaluation values calculated in this manner, the 3D model information representing (visualizing) the difference by the 3D model is supplied to the effect generation unit 265. In addition, among the calculated evaluation values, meta information (a deviation amount, a deviation part, or the like) obtained by converting the difference into a numerical value or a text is supplied to the display control unit 266 and the instruction information generation unit 162 (the device 100 on the teacher side).

(Details of Effect Generation Unit)

Figure 11:
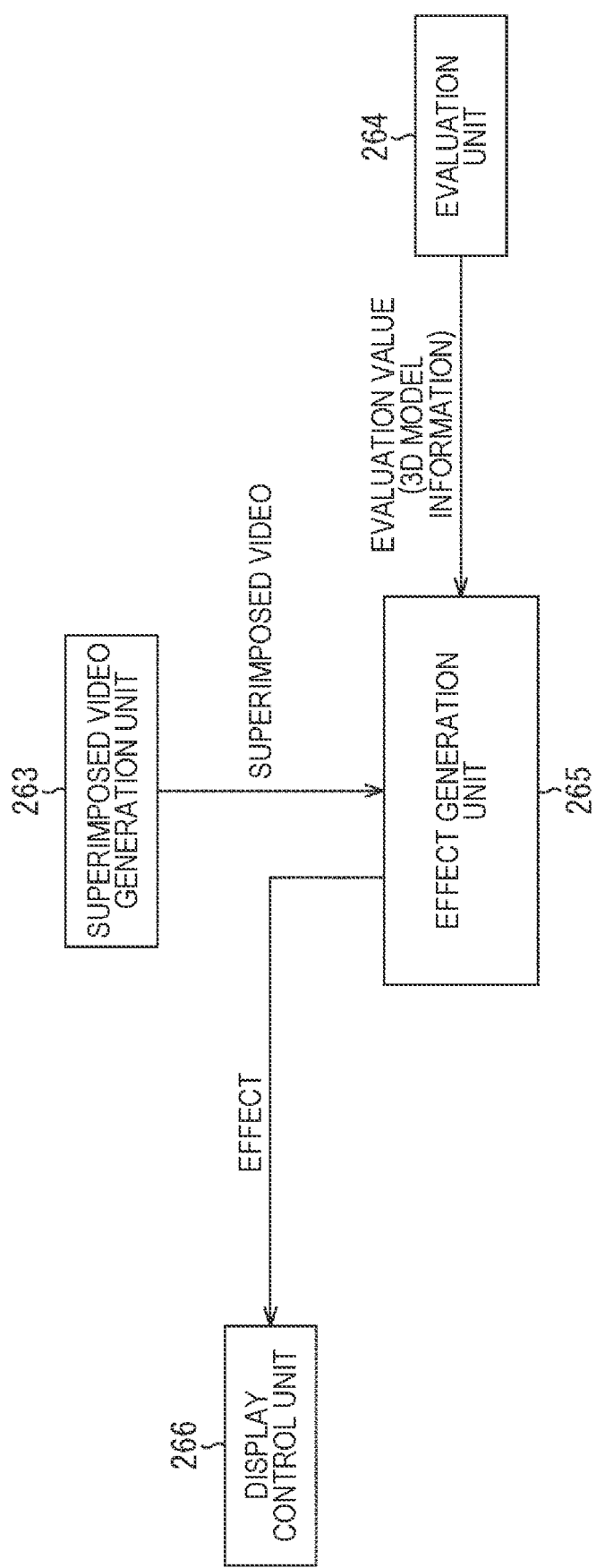
FIG. 11 is a diagram for explaining details of an effect generation unit.

FIG. 11 is a diagram for explaining details of the effect generation unit 265 of the device 200 on the student side.

On the basis of the evaluation value (3D model information) from the evaluation unit 264, the effect generation unit 265 generates an effect video for the superimposed video from the superimposed video generation unit 263. The effect video is, for example, a video for highlighting a part (portion) deviated in the 3D model between the student digital twin and the adjusted teacher digital twin with a predetermined color or texture, a predetermined figure or pattern combined with the background of the student digital twin in a case where there is a deviation, and a line or an afterimage indicating a trajectory of the movement of the student digital twin or the adjusted teacher digital twin.

The effect generation unit 265 maps the effect video to a predetermined reference position on the virtual space, synchronizes the effect video at a predetermined reference time, superimposes the effect video on the superimposed video, and supplies the superimposed video to the display control unit 266.

In the effect video, similarly to the skin data, effect videos having different visual textures are prepared for each purpose of the body motion of the person. That is, the effect generation unit 265 generates an effect video image of a type corresponding to the selected purpose of the body motion. For example, in a case where soccer is selected as the purpose of the body motion, a type of effect video corresponding to soccer is generated, and in a case where aerobics is selected as the purpose of the body motion, a type of effect video corresponding to aerobics is generated.

As described above, the display control unit 266 may cause the display unit 210 to display only the superimposed video from the superimposed video generation unit 263, or may cause the display unit 210 to display the superimposed video on which the effect video is superimposed, from the effect generation unit 265.

Furthermore, in a case where the effect video is displayed on the display unit 210, the display control unit 266 can also switch the effect video displayed on the display unit 210 to an effect video or the like of another texture, for example, in accordance with an operation of the user (student). In this case, a plurality of types of effect videos having different textures is prepared for the purpose of one body motion.

(Operation of Information Processing System)

Next, operations of the device 100 on the teacher side and the device 200 on the student side included in the above-described information processing system will be described.

Figure 12:
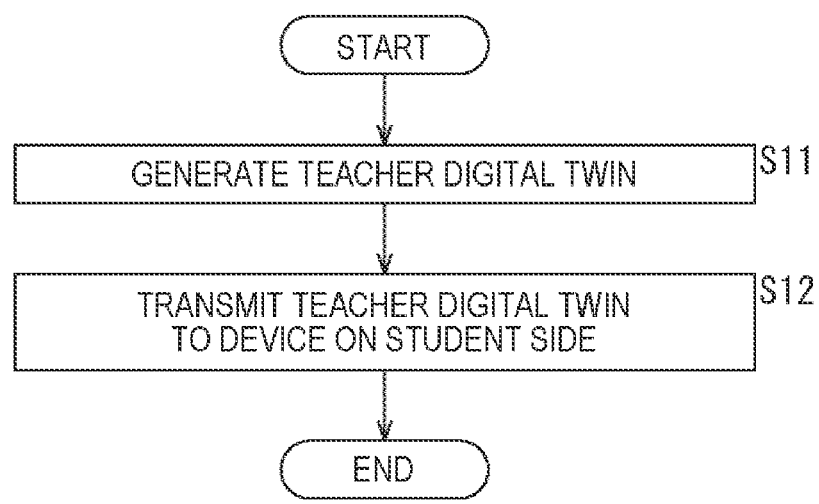
FIG. 12 is a flowchart for explaining an operation of a device on a teacher side.

FIG. 12 is a flowchart for explaining an operation of the device 100 on the teacher side when the teacher is performing in a real-time class, for example. The processing of FIG. 12 is executed, for example, in response to an instruction to start a lesson from a student.

In step S11, the digital twin generation unit 161 generates a teacher digital twin on the basis of sensor data of the teacher sensed by the sensor unit 150.

In step S12, the control unit 160 controls the communication unit 140 to transmit the teacher digital twin generated by the digital twin generation unit 161 to the device 200 on the student side.

Figure 13:
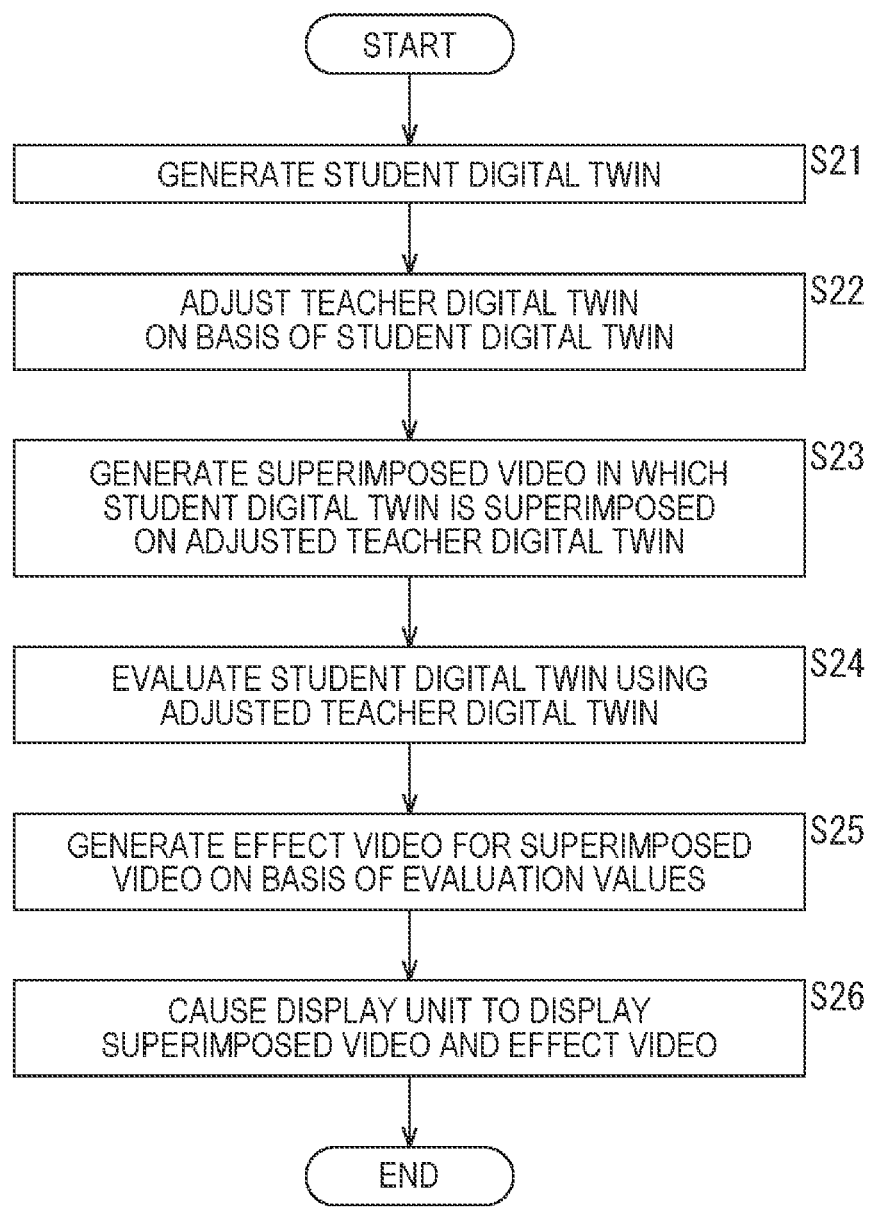
FIG. 13 is a flowchart for explaining an operation of a device on a student side.

FIG. 13 is a flowchart for explaining an operation of the device 200 on the student side when the teacher is performing in a real-time class, for example. The processing of FIG. 13 is executed in conjunction with the processing of FIG. 12.

In step S21, the digital twin generation unit 261 generates a student digital twin on the basis of sensor data of the student sensed by the sensor unit 250.

In step S22, the digital twin adjustment unit 262 generates an adjusted teacher digital twin by adjusting the teacher digital twin from the device 200 on the student side on the basis of the student digital twin generated by the digital twin generation unit 261.

In step S23, the superimposed video generation unit 263 generates a superimposed video in which the student digital twin is superimposed on the adjusted teacher digital twin.

In step S24, the evaluation unit 264 calculates the evaluation value of the student digital twin by evaluating the student digital twin using the adjusted teacher digital twin.

In step S25, the effect generation unit 265 generates an effect video for the superimposed image on the basis of the 3D model information among the evaluation values calculated by the evaluation unit 264.

In step S26, the display control unit 266 causes the display unit 210 to display the superimposed video generated by the superimposed video generation unit 263 and the effect video generated by the effect generation unit 265.

Meanwhile, the meta information among the evaluation values calculated by the evaluation unit 264 is also transmitted to the device 100 on the teacher side.

Figure 14:
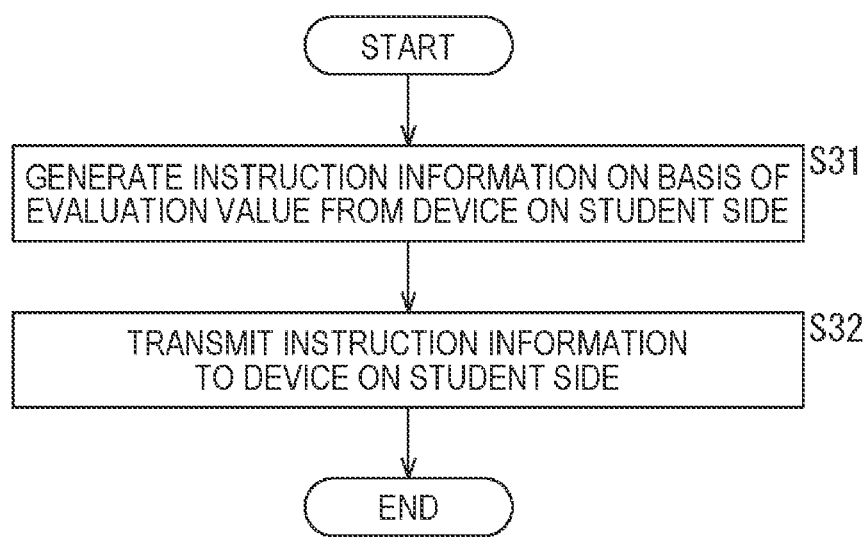
FIG. 14 is a flowchart for explaining an operation of a device on a teacher side.

FIG. 14 is a flowchart for explaining an operation of the device 100 on the teacher side based on the evaluation value from the device 200 on the student side. The processing of FIG. 14 is executed in parallel with the processing of FIG. 13.

In step S31, the instruction information generation unit 162 generates the instruction information on the basis of the evaluation value (meta information) from the device 200 on the student side. Specifically, the instruction information generation unit 162 generates, as the instruction information, display information indicating the deviation amount or the deviation part of the movement of the student with respect to the movement of the teacher. The display information may include a comment automatically generated according to the evaluation value (meta information) or a comment input by the teacher.

In step S32, the control unit 160 controls the communication unit 140 to transmit the instruction information generated by the instruction information generation unit 162 to the device 200 on the student side.

In the device 200 on the student side, the instruction information from the device 100 on the teacher side is displayed on the display unit 210 together with the superimposed video and the effect video by the display control unit 266.

According to the above processing, since the teacher digital twin is adjusted according to the student digital twin, the student can easily copy the movement of the teacher by comparing the own movement with the teacher's movement while watching the superimposed video.

Furthermore, since the effect video based on the difference from the movement of the teacher is superimposed and displayed on the superimposed video, the student can easily recognize the deviation between the own movement and the teacher's movement.

Furthermore, since the instruction information indicating the deviation amount and the deviation part of the movement of the student and the comment corresponding to the deviation amount and the deviation part are displayed together with the effect video, the student can understand how the own movement is specifically deviated and how to move.

As described above, it is possible to provide more effective learning content for the student to learn the movement of the body.

Note that, in the above description, only the evaluation value calculated by the evaluation unit 264 is transmitted from the device 200 on the student side to the device 100 on the teacher side. Alternatively, the superimposed video generated by the superimposed video generation unit 263 and the effect video generated by the effect generation unit 265 may be transmitted from the device 200 on the student side to the device 100 on the teacher side. In this case, in the device 100 on the teacher side, the superimposed video and the effect video are displayed on the display unit 110 under the control of the control unit 160.

As a result, the teacher can easily recognize the deviation between the movement of the teacher and the movement of the student, and can present a more appropriate instruction or advice to the student as the instruction information (comment). Note that the comment for the student may be not only presented as character information but also output as voice information.

3. Application Example of 5G Network Slicing

As described above, in the information processing system to which the technology according to the present disclosure is applied, 5G can be applied as a communication method between devices.

The 5G has three features of "high speed and large capacity", "low latency", and "multiple simultaneous connection". These functions can be implemented by a technology called network slicing for virtually dividing (slicing) a network. In 5G, data can be transmitted in a high-speed large-capacity network slice (hereinafter, simply referred to as a slice.) or can be transmitted in a low-latency network slice according to the type and application of data.

(3-1. Application Example of 5G Network Slicing 1)

Hereinafter, an application example of 5G network slicing applied to an information processing system to which the technology according to the present disclosure is applied will be described.

(3-1-1. Device-Device Configuration 1)

Figure 15:
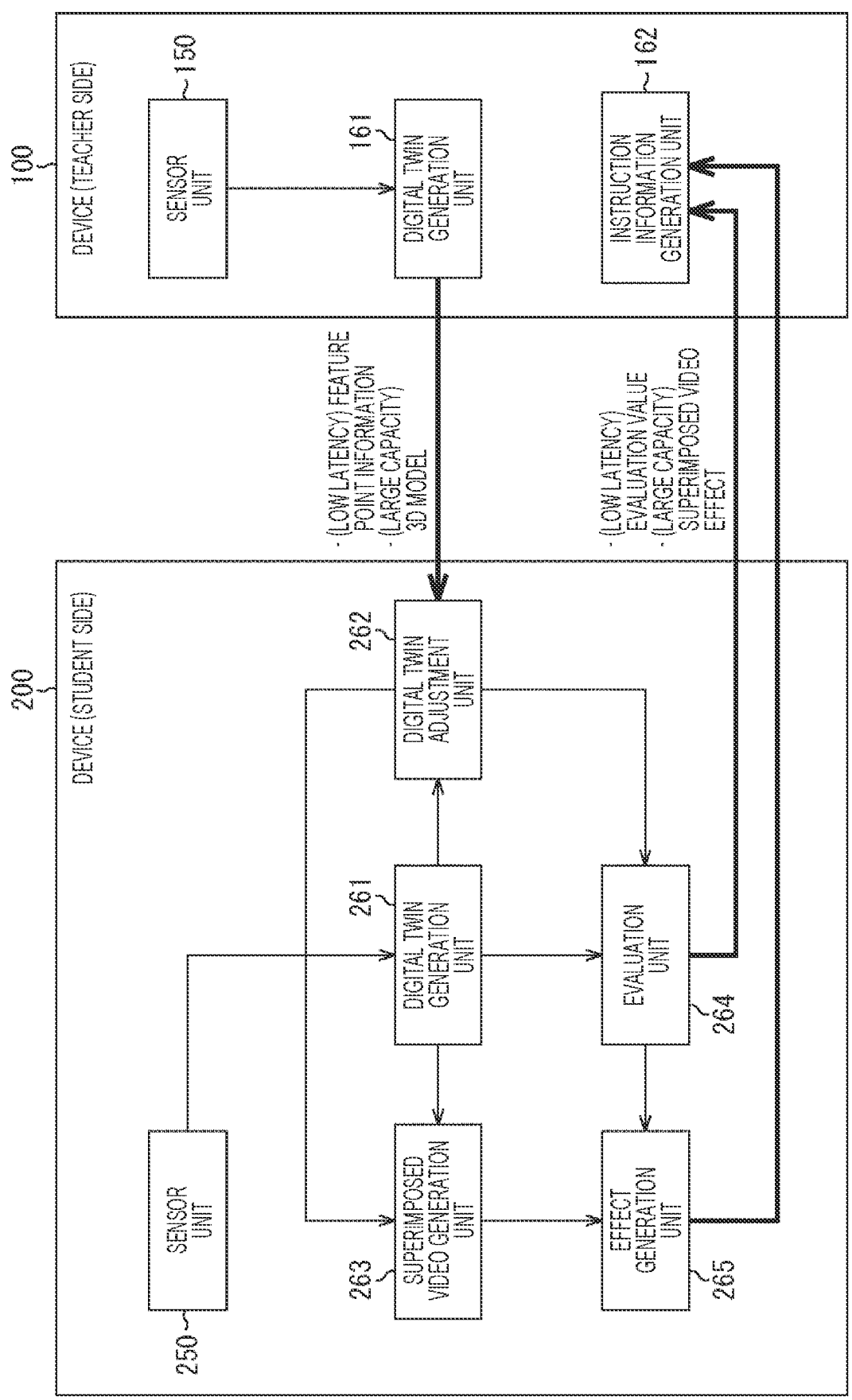
FIG. 15 is a diagram illustrating an application example of 5G network slicing.

FIG. 15 is a diagram illustrating an example in which 5G network slicing is applied to the information processing system described above. In the drawing, bold line arrows indicate transmission paths supported by 5G.

In the example of FIG. 15, in the teacher digital twin generated by the digital twin generation unit 161, from the teacher side to the student side (the digital twin adjustment unit 262), the feature point information is transmitted via a low latency slice, and the 3D model is transmitted via a large-capacity slice.

Furthermore, from the student side to the teacher side (instruction information generation unit 162), the evaluation value calculated by the evaluation unit 264 is transmitted via a low latency slice, and the superimposed video generated by the superimposed video generation unit 263 and the effect video generated by the effect generation unit 265 are transmitted via a large-capacity slice.

In this case, the instruction information generation unit 162 may generate the instruction information for the student on the basis of the superimposed video from the superimposed video generation unit 263 or the effect video from the effect generation unit 265. Furthermore, the superimposed video and the effect video supplied to the instruction information generation unit 162 may be displayed on the display unit 110 under the control of the control unit 160.

As described above, since the feature point information and the evaluation value required for the real-time property are transmitted via the low latency slice, the followability of the digital twin with respect to the body motion of the teacher and the quickness of the feedback regarding the body motion of the student can be secured.

Incidentally, each functional unit included in the control unit 160 and each functional unit included in the control unit 260 described above may not be implemented on the device 100 on the teacher side and the device 200 on the student side, respectively.

(3-1-2. Device-Device Configuration 2)

Figure 16:
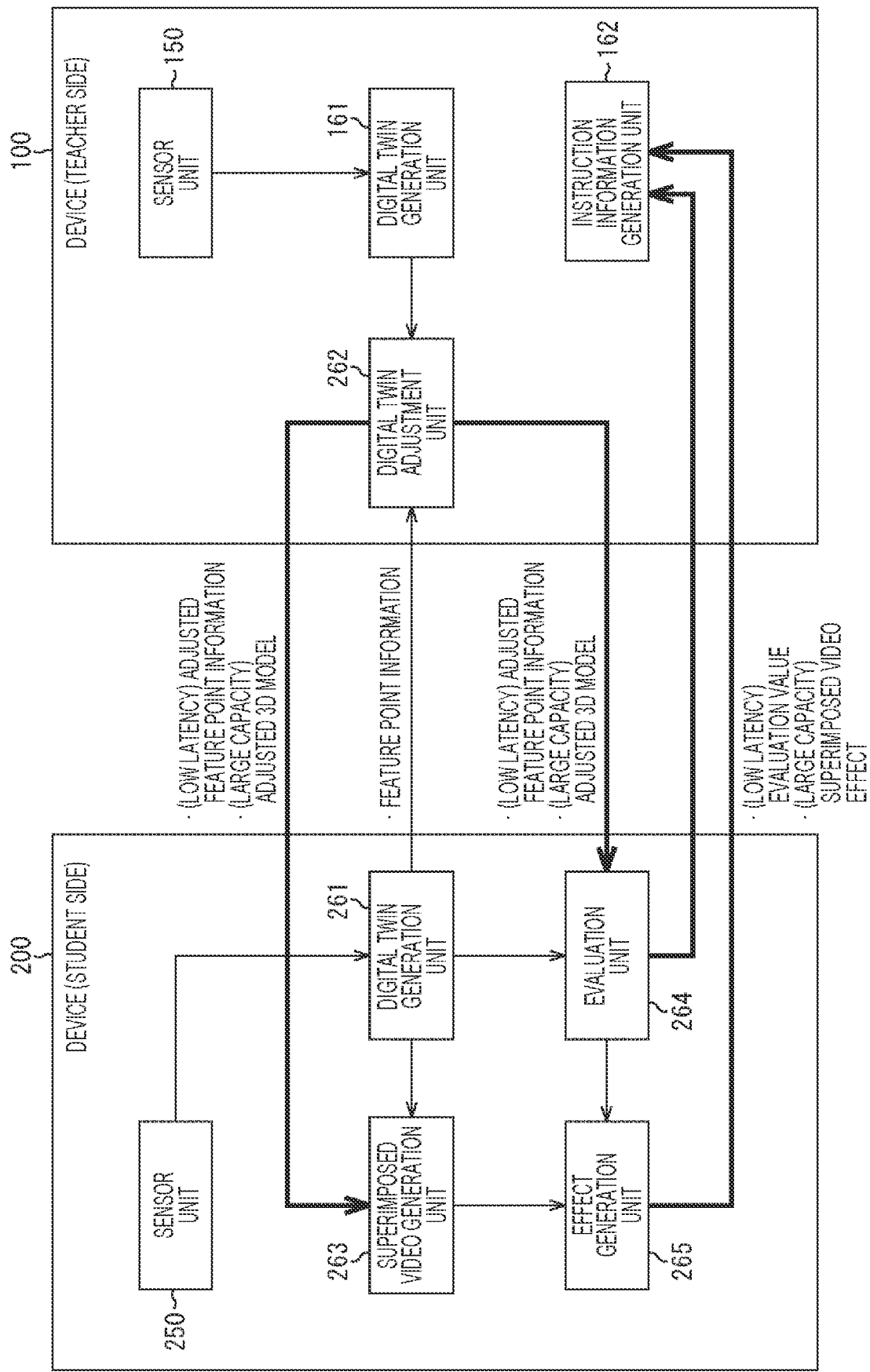
FIG. 16 is a diagram illustrating an application example of 5G network slicing.

As illustrated in FIG. 16, the digital twin adjustment unit 262 may be implemented on the device 100 on the teacher side.

In the example of FIG. 16, from the teacher side to the student side (the superimposed video generation unit 263 and the evaluation unit 264), among the adjusted teacher digital twin generated by the digital twin adjustment unit 262, the adjusted feature point information is transmitted via a low latency slice, and the adjusted 3D model is transmitted via a large-capacity slice.

Furthermore, from the student side to the teacher side (instruction information generation unit 162), the evaluation value calculated by the evaluation unit 264 is transmitted via a low latency slice, and the superimposed video generated by the superimposed video generation unit 263 and the effect video generated by the effect generation unit 265 are transmitted via a large-capacity slice. Note that the feature point information of the student digital twin generated by the digital twin generation unit 261 may be transmitted to the teacher side (the digital twin adjustment unit 262) via a low latency slice.

Although examples in which the digital twin adjustment unit 262 is implemented on either the device 100 on the teacher side or the device 200 on the student side have been described above, it may be implemented on both the devices 100, and 200. Furthermore, the function of the device 100 on the teacher side and the function of the device 200 on the student side may be switched at a predetermined timing.

(3-1-3. Device-MEC-Device Configuration 1)

Figure 17:
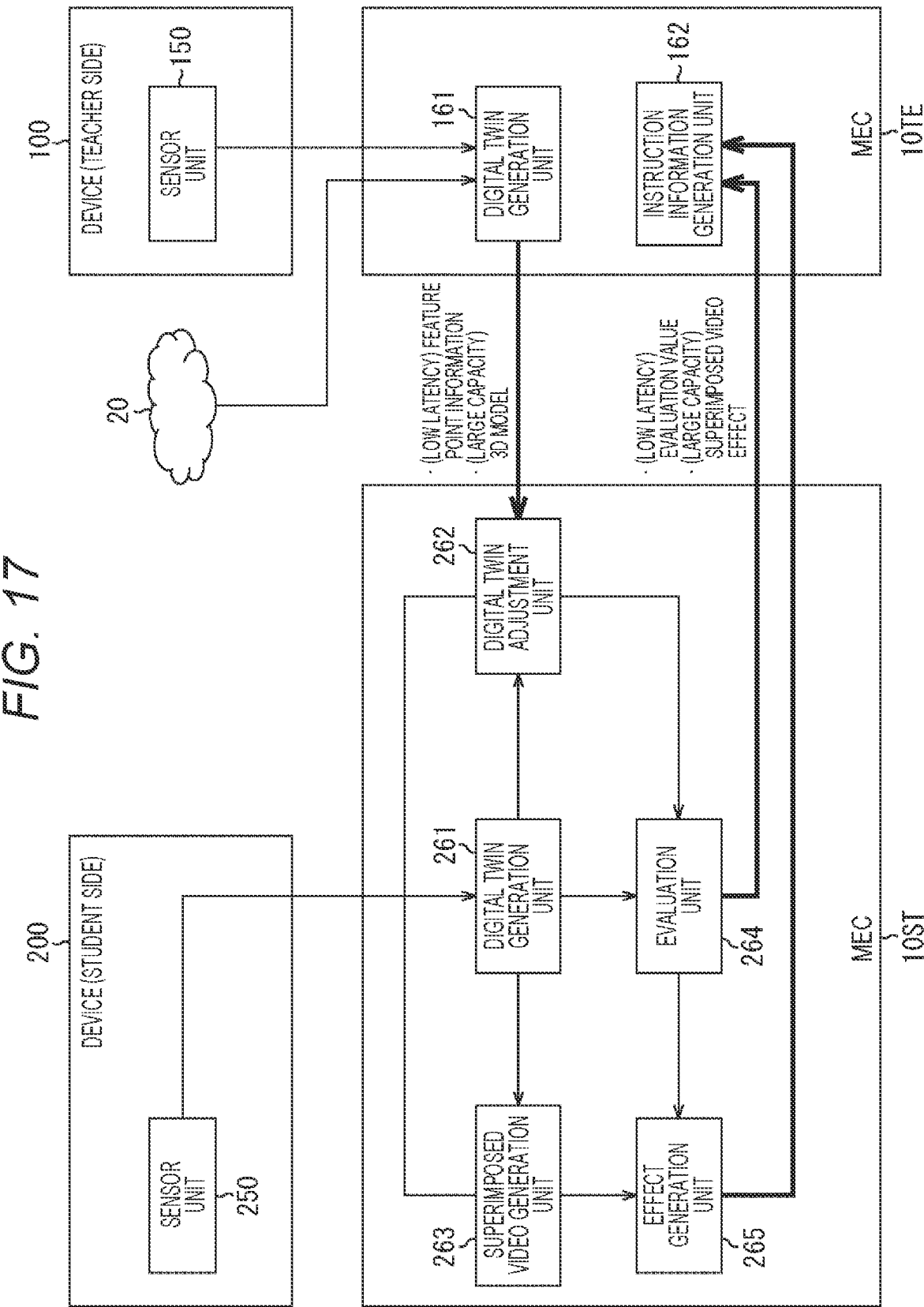
FIG. 17 is a diagram illustrating an application example of 5G network slicing.

As illustrated in FIG. 17, the digital twin generation unit 161 and the instruction information generation unit 162 may be implemented on a MEC server 10TE close to the device 100 on the teacher side, and the digital twin generation unit 261 to the effect generation unit 265 may be implemented on a MEC server 10ST close to the device 200 on the student side.

In this case, the device 100 on the teacher side transmits the sensing data acquired by the sensor unit 150 to the MEC server 10TE (the digital twin generation unit 161). Similarly, the device 200 on the student side transmits the sensing data acquired by the sensor unit 250 to the MEC server 10ST (the MEC server 10ST).

Note that the MEC server 10TE (the digital twin generation unit 161) may generate the teacher digital twin by extracting feature points from the recoded content stored in the cloud server 20. As a result, the use case UC2 and the use case UC4 in FIG. 4 are implemented.

In the example of FIG. 17, in the teacher digital twin generated by the digital twin generation unit 161, from the MEC server 10TE on the teacher side to the MEC server 10ST (the digital twin adjustment unit 262) on the student side, the feature point information is transmitted via a low latency slice, and the 3D model is transmitted via a large-capacity slice.

Furthermore, from the MEC server 10ST on the student side to the MEC server 10TE (the instruction information generation unit 162) on the teacher side, the evaluation value calculated by the evaluation unit 264 is transmitted via a low latency slice, and the superimposed video generated by the superimposed video generation unit 263 and the effect video generated by the effect generation unit 265 are transmitted via a large-capacity slice.

(3-1-4. Device-MEC-Device Configuration 2)

Figure 18:
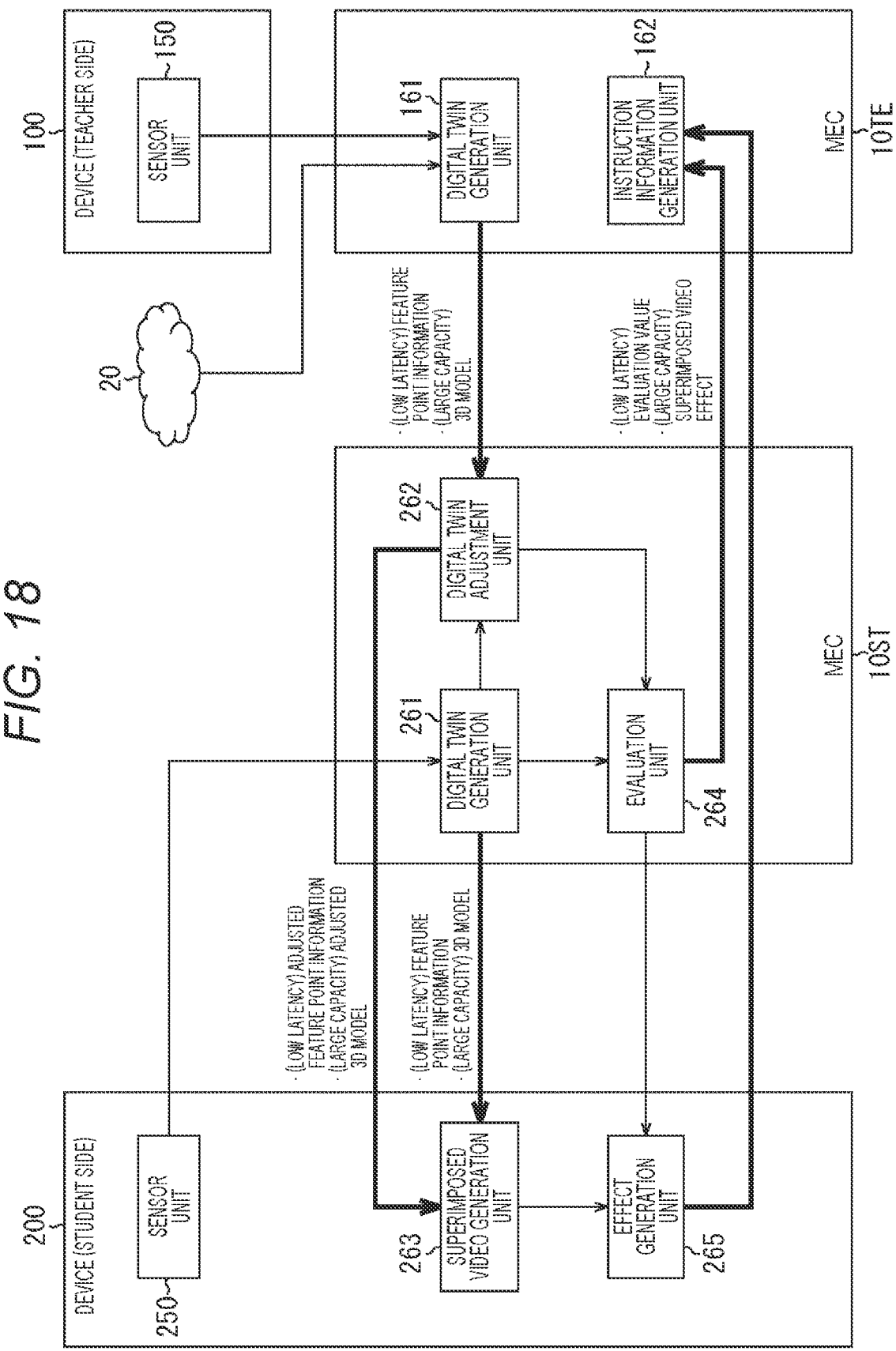
FIG. 18 is a diagram illustrating an application example of 5G network slicing.

As illustrated in FIG. 18, the digital twin generation unit 161 and the instruction information generation unit 162 may be implemented on the MEC server 10TE close to the device 100 on the teacher side, and the digital twin generation unit 261, the digital twin adjustment unit 262, and the evaluation unit 264 may be implemented on a MEC server 10ST close to the device 200 on the student side.

In the example of FIG. 18, in the teacher digital twin generated by the digital twin generation unit 161, from the MEC server 10TE on the teacher side to the MEC server 10ST (the digital twin adjustment unit 262) on the student side, the feature point information is transmitted via a low latency slice, and the 3D model is transmitted via a large-capacity slice.

In the student digital twin generated by the digital twin generation unit 261, from the MEC server 10ST on the student side to the device 200 (the superimposed video generation unit 263) on the student side, the feature point information is transmitted via a low latency slice, and the 3D model is transmitted via a large-capacity slice. Similarly, to the device 200 (the superimposed video generation unit 263) on the student side, among the adjusted teacher digital twin generated by the digital twin adjustment unit 262, the adjusted feature point information is transmitted via a low latency slice, and the adjusted 3D model is transmitted via a large-capacity slice.

In addition, the evaluation value calculated by the evaluation unit 264 is transmitted from the MEC server 10ST on the student side to the MEC server 10TE (the instruction information generation unit 162) on the teacher side via a low latency slice. Furthermore, from the device 200 on the student side to the MEC server 10TE (the instruction information generation unit 162) on the teacher side, the superimposed video generated by the superimposed video generation unit 263 and the effect video generated by the effect generation unit 265 are transmitted via a large-capacity slice.

(3-1-5. Device-MEC-Device Configuration 3)

Figure 19:
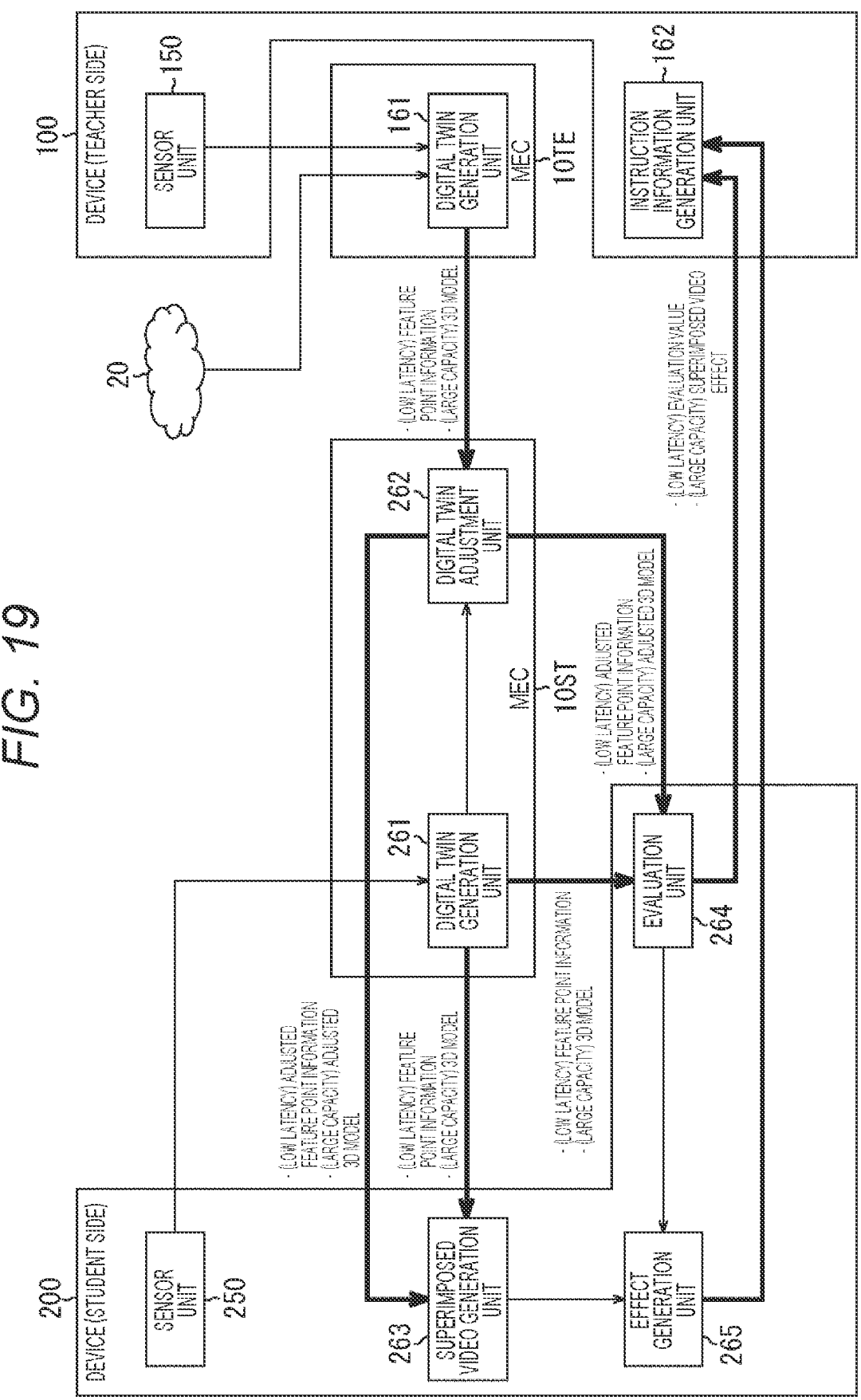
FIG. 19 is a diagram illustrating an application example of 5G network slicing.

As illustrated in FIG. 19, the digital twin generation unit 161 may be realized on the MEC server 10TE close to the device 100 on the teacher side, and the digital twin generation unit 261 and the digital twin adjustment unit 262 may be realized on a MEC server 10ST close to the device 200 on the student side.

In the example of FIG. 19, in the teacher digital twin generated by the digital twin generation unit 161, from the MEC server 10TE on the teacher side to the MEC server 10ST (the digital twin adjustment unit 262) on the student side, the feature point information is transmitted via a low latency slice, and the 3D model is transmitted via a large-capacity slice.

In the student digital twin generated by the digital twin generation unit 261, from the MEC server 10ST on the student side to the device 200 (the superimposed video generation unit 263 and the evaluation unit 264) on the student side, the feature point information is transmitted via a low latency slice, and the 3D model is transmitted via a large-capacity slice. Similarly, to the device 200 (the superimposed video generation unit 263 and the evaluation unit 264) on the student side, among the adjusted teacher digital twin generated by the digital twin adjustment unit 262, the adjusted feature point information is transmitted via a low latency slice, and the adjusted 3D model is transmitted via a large-capacity slice.

Furthermore, from the device 200 on the student side to the device 100 (instruction information generation unit 162) on the teacher side, the evaluation value calculated by the evaluation unit 264 is transmitted via a low latency slice, and the superimposed video generated by the superimposed video generation unit 263 and the effect video generated by the effect generation unit 265 are transmitted via a large-capacity slice.

(3-1-6. Device-MEC-Device Configuration 4)

Figure 20:
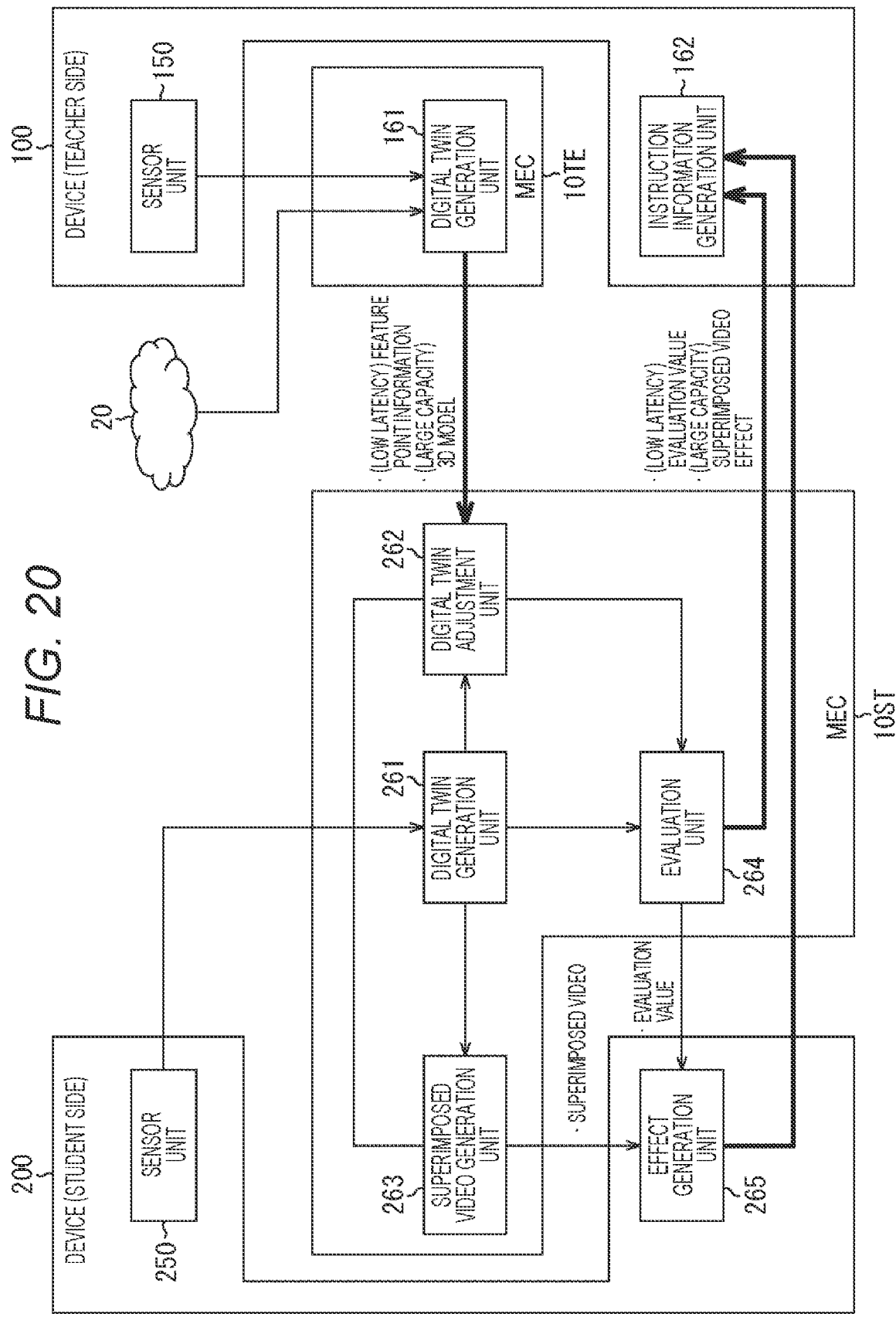
FIG. 20 is a diagram illustrating an application example of 5G network slicing.

As illustrated in FIG. 20, the digital twin generation unit 161 may be implemented on the MEC server 10TE close to the device 100 on the teacher side, and the digital twin generation unit 261 to the evaluation unit 264 may be implemented on a MEC server 10ST close to the device 200 on the student side.

In the example of FIG. 20, in the teacher digital twin generated by the digital twin generation unit 161, from the MEC server 10TE on the teacher side to the MEC server 10ST (the digital twin adjustment unit 262) on the student side, the feature point information is transmitted via a low latency slice, and the 3D model is transmitted via a large-capacity slice.

In addition, the evaluation value calculated by the evaluation unit 264 is transmitted from the MEC server 10ST on the student side to the device 100 (the instruction information generation unit 162) on the teacher side via a low latency slice. Furthermore, from the device 200 on the student side to the device 100 (the instruction information generation unit 162) on the teacher side, the superimposed video generated by the superimposed video generation unit 263 and the effect video generated by the effect generation unit 265 are transmitted via a large-capacity slice.

Note that the superimposed video generated by the superimposed video generation unit 263 may be transmitted from the MEC server 10ST on the student side to the device 200 (the effect generation unit 265) on the student side via a large-capacity slice. Furthermore, the evaluation value (3D model information) calculated by the evaluation unit 264 may be transmitted from the MEC server 10ST on the student side to the device 200 (the effect generation unit 265) on the student side via a large-capacity slice.

(3-1-7. Device-MEC-Device Configuration 5)

Figure 21:
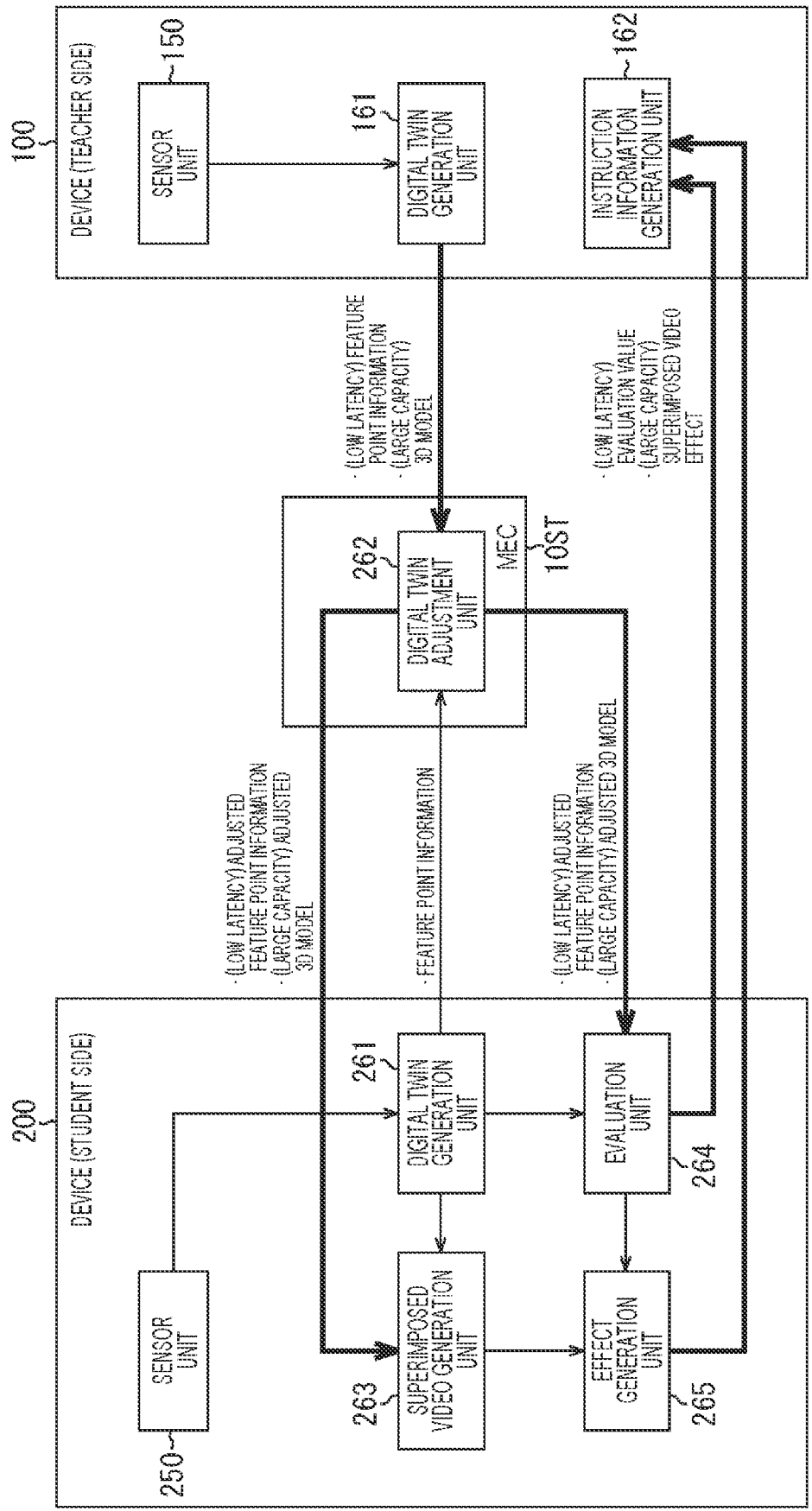
FIG. 21 is a diagram illustrating an application example of 5G network slicing.

As illustrated in FIG. 21, only the digital twin adjustment unit 262 may be implemented on the MEC server 10ST close to the device 200 on the student side.

In the example of FIG. 21, in the teacher digital twin generated by the digital twin generation unit 161, from the device 100 on the teacher side to the MEC server 10ST (the digital twin adjustment unit 262) on the student side, the feature point information is transmitted via a low latency slice, and the 3D model is transmitted via a large-capacity slice.

From the MEC server 10ST on the student side, to the device 200 (the superimposed video generation unit 263 and the evaluation unit 264) on the student side, among the adjusted teacher digital twin generated by the digital twin adjustment unit 262, the adjusted feature point information is transmitted via a low latency slice, and the adjusted 3D model is transmitted via a large-capacity slice.

Furthermore, from the device 200 on the student side to the device 100 (instruction information generation unit 162) on the teacher side, the evaluation value calculated by the evaluation unit 264 is transmitted via a low latency slice, and the superimposed video generated by the superimposed video generation unit 263 and the effect video generated by the effect generation unit 265 are transmitted via a large-capacity slice.

Note that the feature point information of the student digital twin generated by the digital twin generation unit 261 may be transmitted to the MEC server 10ST (the digital twin adjustment unit 262) on the student side via a low latency slice.

In the example of FIG. 21, the digital twin adjustment unit 262 is implemented on the MEC server 10ST close to the device 200 on the student side, but may be implemented on the MEC server 10TE close to the device 100 on the teacher side.

(3-2. Other Configuration Examples of Information Processing System)

The configuration of the information processing system that realizes the real-time class has been mainly described above. On the other hand, if the teacher digital twin generated in advance can be reproduced, the user (student) at home can take a non-real-time lesson at a desired timing instead of a real-time class.

Figure 22:
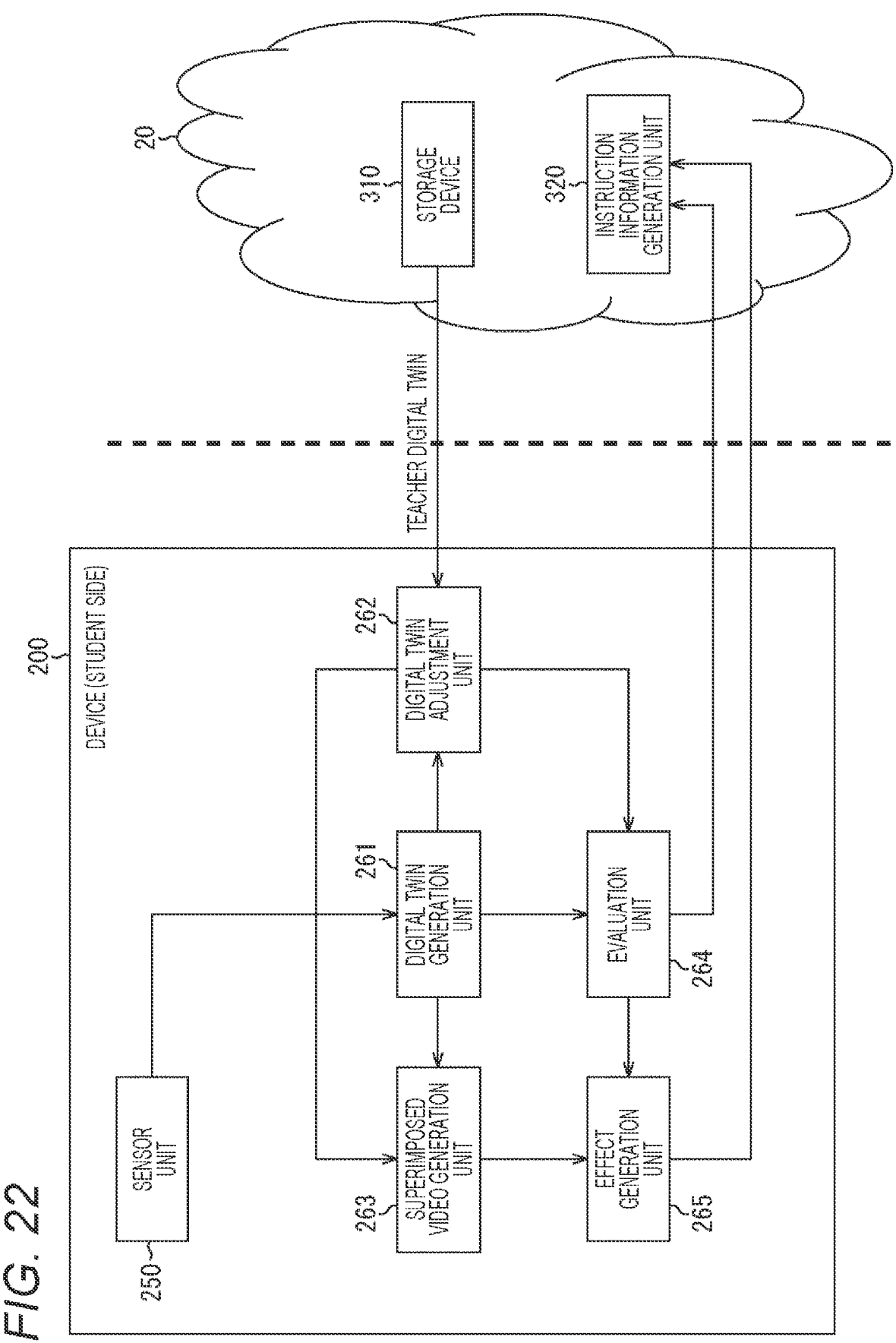
FIG. 22 is a block diagram illustrating another functional configuration example of the information processing system.

FIG. 22 is a block diagram illustrating another configuration example of an information processing system to which the technology according to the present disclosure is applied.

The information processing system in FIG. 22 includes a cloud server 20 and a device 200 on the student side. The device 200 on the student side in FIG. 22 is configured similarly to the device 200 on the student side described above, but only main functional units are illustrated in FIG. 22.

The cloud server 20 includes a storage device 310 and an instruction information generation unit 320.

The storage device 310 stores the teacher digital twin generated in advance, and supplies the teacher digital twin to the device 200 on the student side in response to a request from the device 200 on the student side.

The instruction information generation unit 320 basically has a function similar to that of the instruction information generation unit 162 described above, but is different from the instruction information generation unit 162 in that the instruction information is automatically generated on the basis of artificial intelligence (AI).

Figure 23:
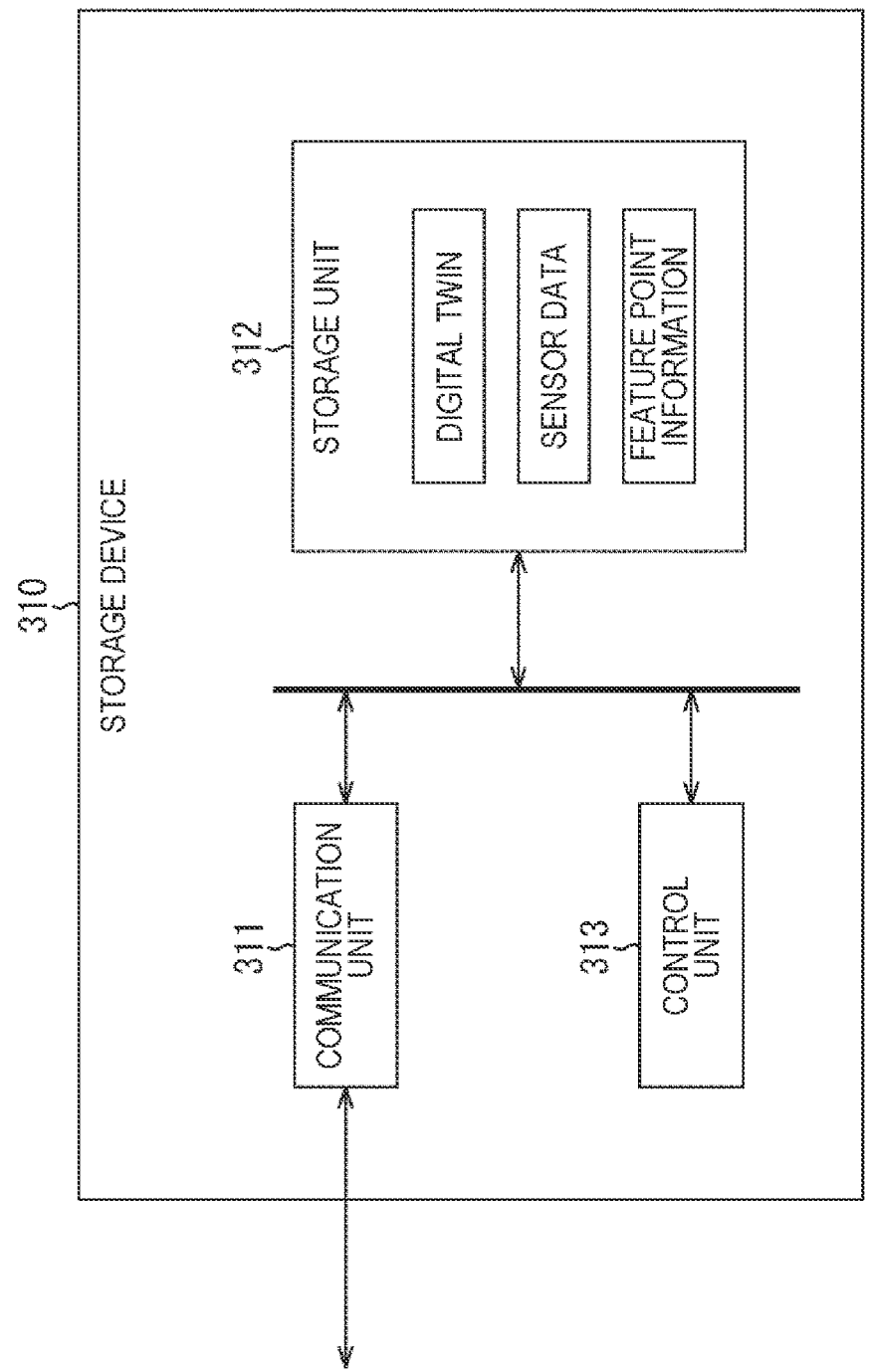
FIG. 23 is a diagram for explaining details of a storage device.

FIG. 23 is a diagram for explaining details of the storage device 310.

As illustrated in FIG. 23, the storage device 310 includes a communication unit 311, a storage unit 312, and a control unit 313.

The communication unit 311 includes a network interface and the like, and communicates with the device 200 on the student side on the basis of the control of the control unit 313.

The storage unit 312 stores programs necessary for operating the storage device 310, various data prepared in advance, and the like.

Specifically, the storage unit 312 stores the real-time performance of the person and the teacher digital twin generated on the basis of the recoded content, and the stored teacher digital twin is read in response to a request from the device 200 on the student side.

Furthermore, the storage unit 312 may store sensor data and feature point information acquired in advance, and the teacher digital twin may be generated on the basis of the sensor data and the feature point information. Furthermore, a predetermined recoded content may be stored in the storage unit 312, and the teacher digital twin may be generated on the basis of the recoded content.

The control unit 313 executes various processing on the basis of the program stored in the storage unit 312. For example, in response to a request from the device 200 on the student side, the control unit 313 supplies the teacher digital twin stored in the storage unit 312 to the device 200 on the student side, and generates the teacher digital twin on the basis of the sensor data and the feature point information stored in the storage unit 312.

Also in the above configuration, since the teacher digital twin is adjusted according to the student digital twin, the student can easily copy the movement of the teacher by comparing the own movement with the teacher's movement while watching the superimposed video.

Furthermore, since the effect video based on the difference from the movement of the teacher is superimposed and displayed on the superimposed video, the student can easily recognize the deviation between the own movement and the teacher's movement.

Furthermore, since the instruction information indicating the deviation amount and the deviation part of the movement of the student and the comment corresponding to the deviation amount and the deviation part are displayed together with the effect video, the student can understand how the own movement is specifically deviated and how to move.

As described above, it is possible to provide more effective learning content for the student to learn the movement of the body.

Note that, in the storage device 310, the teacher digital twin, the sensor data, and the feature point information stored in the storage device 310 may be managed in association with the person who has performed the body motion reflected in the digital twin, the sensor data, and the feature point information. Furthermore, in the storage device 310, for example, feature point information may be extracted from a game video of a professional soccer player, and a teacher digital twin generated on the basis of skeleton estimation using machine learning or the like may be managed in association with the professional soccer player.

For example, a person ID for specifying a certain person, time information indicating the date and time when the digital twin is generated, genre information indicating the purpose and type of the body motion, and the like are associated with the digital twin reflecting the body motion of the certain person.

As a result, the user to be a student can select a desired person or a digital twin of body motion and take a non-real-time lesson.

Furthermore, the digital twin associated with the person ID may be a target of electronic commerce in a marketplace (electronic market). In this case, in the storage device 310, the metadata of the copyright information including the person ID, the sales price, the sales period, and the like of the digital twin is stored as a database and centrally managed.

As a result, it is possible to manage the copyright of the provider of the digital twin, for example, protecting the provider's own movement such as an instructor who has provided the digital twin as a work or entering a license agreement by the provider with a predetermined company or group.

(3-3. Application Example of 5G Network Slicing 2)

The 5G network slicing can also be applied to the information processing system of FIG. 22.

(3-3-1. Device-MEC-Cloud Configuration 1)

Figure 24:
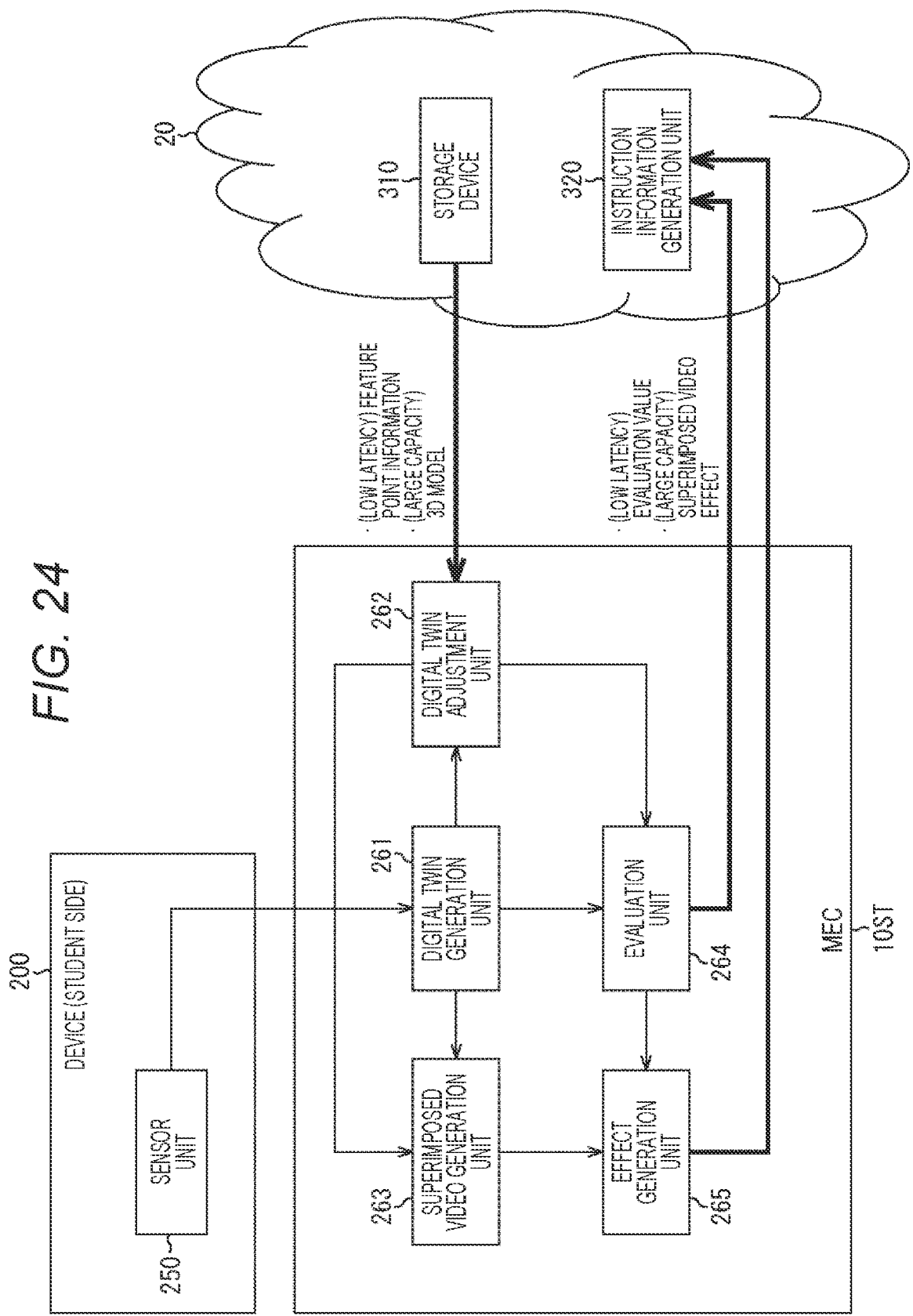
FIG. 24 is a diagram illustrating an application example of 5G network slicing.

FIG. 24 is a diagram illustrating an example in which 5G network slicing is applied to the information processing system of FIG. 22. In the drawing, bold line arrows indicate transmission paths supported by 5G.

In the example of FIG. 24, the digital twin generation unit 261 to the effect generation unit 265 are implemented on the MEC server 10ST close to the device 200 on the student side.

In this case, the device 200 on the student side transmits the sensing data acquired by the sensor unit 250 to the MEC server 10ST (the digital twin generation unit 261).

In the example of FIG. 24, in the teacher digital twin stored in the storage device 310, from the cloud server 20 to the MEC server 10ST (the digital twin adjustment unit 262) on the student side, the feature point information is transmitted via a low latency slice, and the 3D model is transmitted via a large-capacity slice.

Furthermore, from the MEC server 10ST on the student side to the cloud server 20 (the instruction information generation unit 320), the evaluation value calculated by the evaluation unit 264 is transmitted via a low latency slice, and the superimposed video generated by the superimposed video generation unit 263 and the effect video generated by the effect generation unit 265 are transmitted via a large-capacity slice.

(3-3-2. Device-MEC-Cloud Configuration 2)

Figure 25:
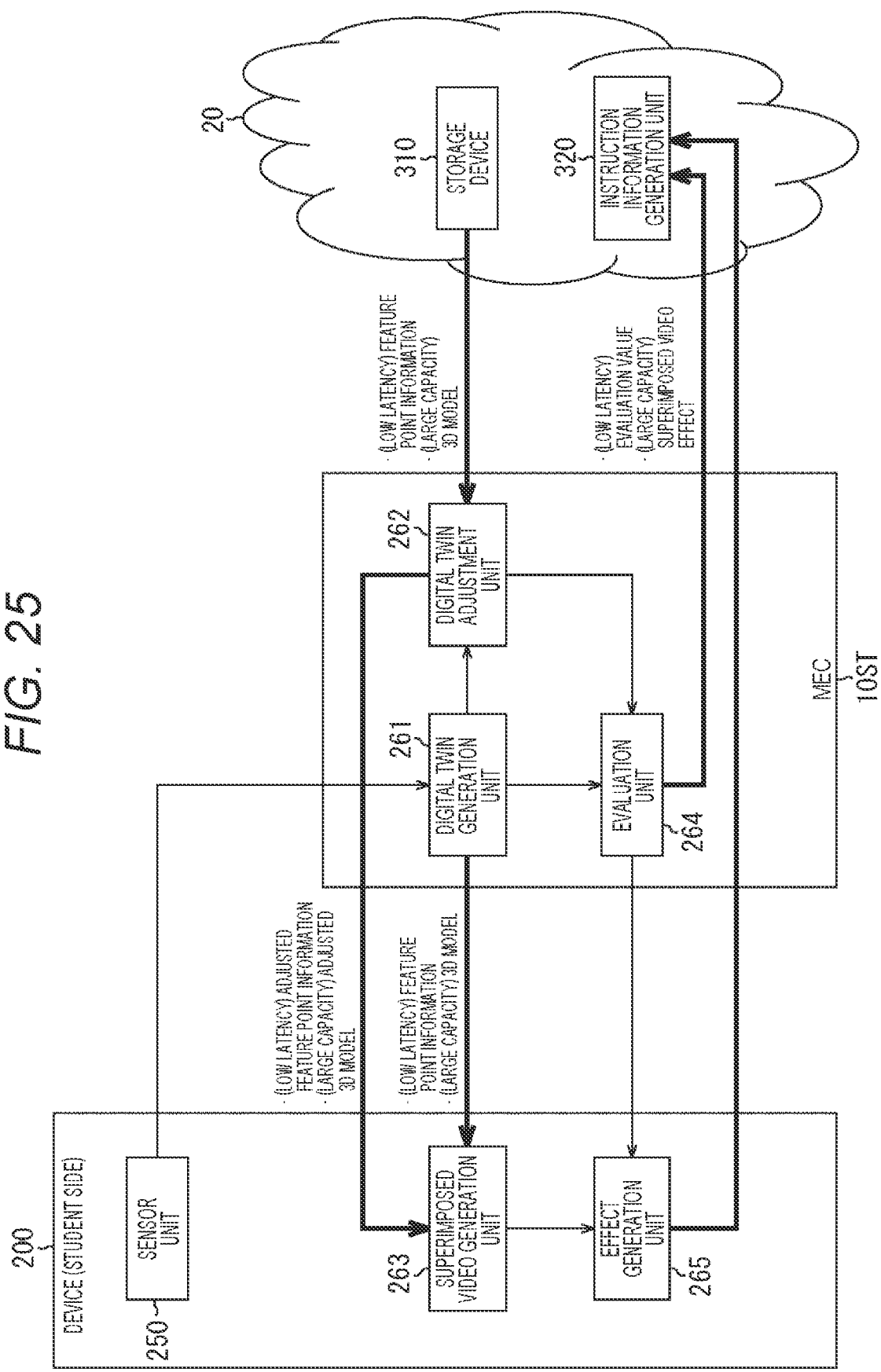
FIG. 25 is a diagram illustrating an application example of 5G network slicing.

As illustrated in FIG. 25, the digital twin generation unit 261, the digital twin adjustment unit 262, and the evaluation unit 264 may be implemented on the MEC server 10ST close to the device 200 on the student side.

In the example of FIG. 25, in the teacher digital twin stored in the storage device 310, from the cloud server 20 to the MEC server 10ST (the digital twin adjustment unit 262) on the student side, the feature point information is transmitted via a low latency slice, and the 3D model is transmitted via a large-capacity slice.

In the student digital twin generated by the digital twin generation unit 261, from the MEC server 10ST on the student side to the device 200 (the superimposed video generation unit 263) on the student side, the feature point information is transmitted via a low latency slice, and the 3D model is transmitted via a large-capacity slice. Similarly, to the device 200 (the superimposed video generation unit 263) on the student side, among the adjusted teacher digital twin generated by the digital twin adjustment unit 262, the adjusted feature point information is transmitted via a low latency slice, and the adjusted 3D model is transmitted via a large-capacity slice.

In addition, the evaluation value calculated by the evaluation unit 264 is transmitted from the MEC server 10ST on the student side to the cloud server 20 (the instruction information generation unit 320) via a low latency slice. Furthermore, from the device 200 on the student side to the cloud server 20 (the instruction information generation unit 320), the superimposed video generated by the superimposed video generation unit 263 and the effect video generated by the effect generation unit 265 are transmitted via a large-capacity slice.

(3-3-3. Device-MEC-Cloud Configuration 3)

Figure 26:
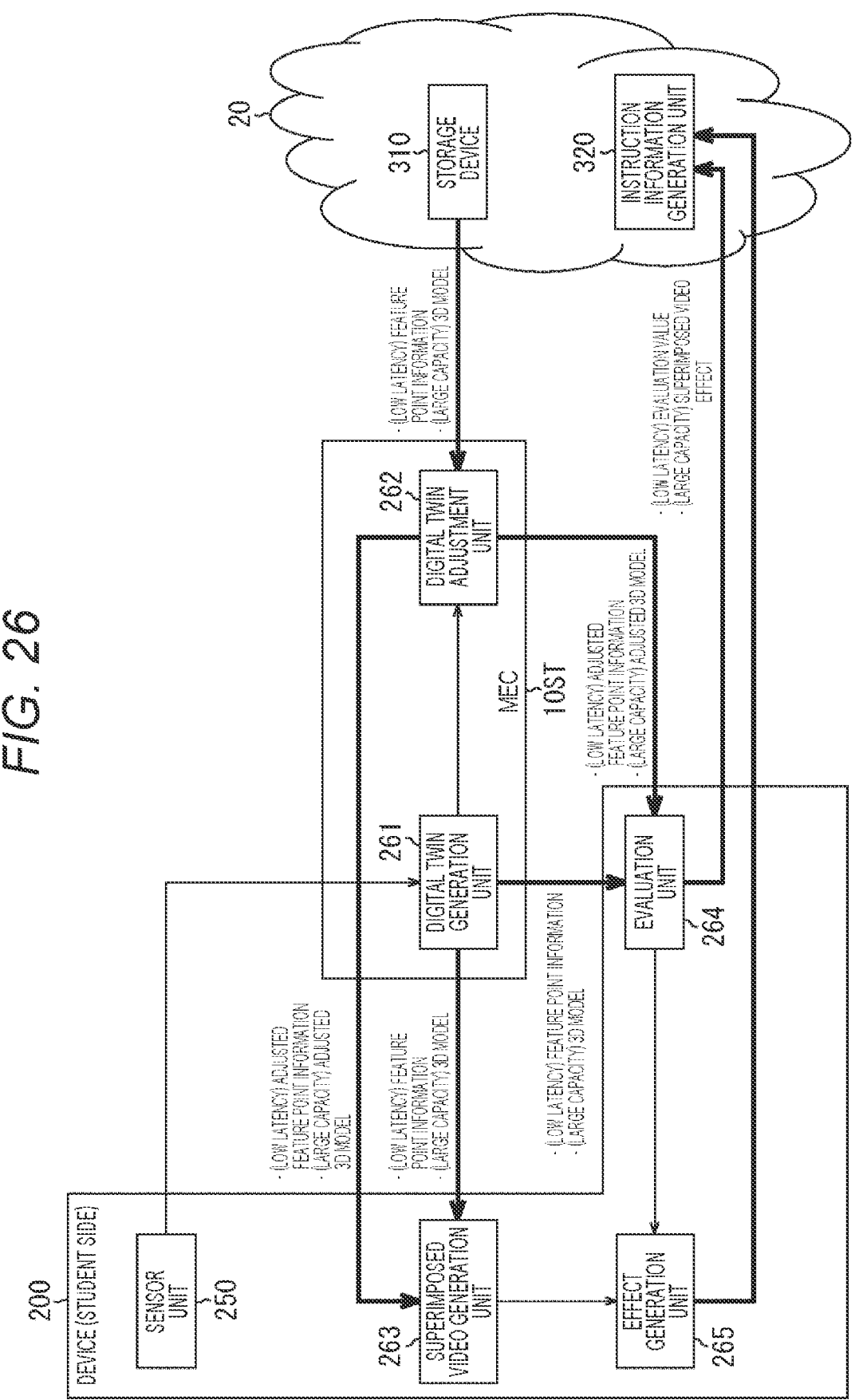
FIG. 26 is a diagram illustrating an application example of 5G network slicing.

As illustrated in FIG. 26, the digital twin generation unit 261 and the digital twin adjustment unit 262 may be implemented on the MEC server 10ST close to the device 200 on the student side.

In the example of FIG. 26, in the teacher digital twin stored in the storage device 310, from the cloud server 20 to the MEC server 10ST (the digital twin adjustment unit 262) on the student side, the feature point information is transmitted via a low latency slice, and the 3D model is transmitted via a large-capacity slice.

In the student digital twin generated by the digital twin generation unit 261, from the MEC server 10ST on the student side to the device 200 (the superimposed video generation unit 263 and the evaluation unit 264) on the student side, the feature point information is transmitted via a low latency slice, and the 3D model is transmitted via a large-capacity slice. Similarly, to the device 200 (the superimposed video generation unit 263 and the evaluation unit 264) on the student side, among the adjusted teacher digital twin generated by the digital twin adjustment unit 262, the adjusted feature point information is transmitted via a low latency slice, and the adjusted 3D model is transmitted via a large-capacity slice.

Furthermore, from the device 200 on the student side to the cloud server 20 (the instruction information generation unit 320), the evaluation value calculated by the evaluation unit 264 is transmitted via a low latency slice, and the superimposed video generated by the superimposed video generation unit 263 and the effect video generated by the effect generation unit 265 are transmitted via a large-capacity slice.

(3-3-4. Device-MEC-Cloud Configuration 4)

Figure 27:
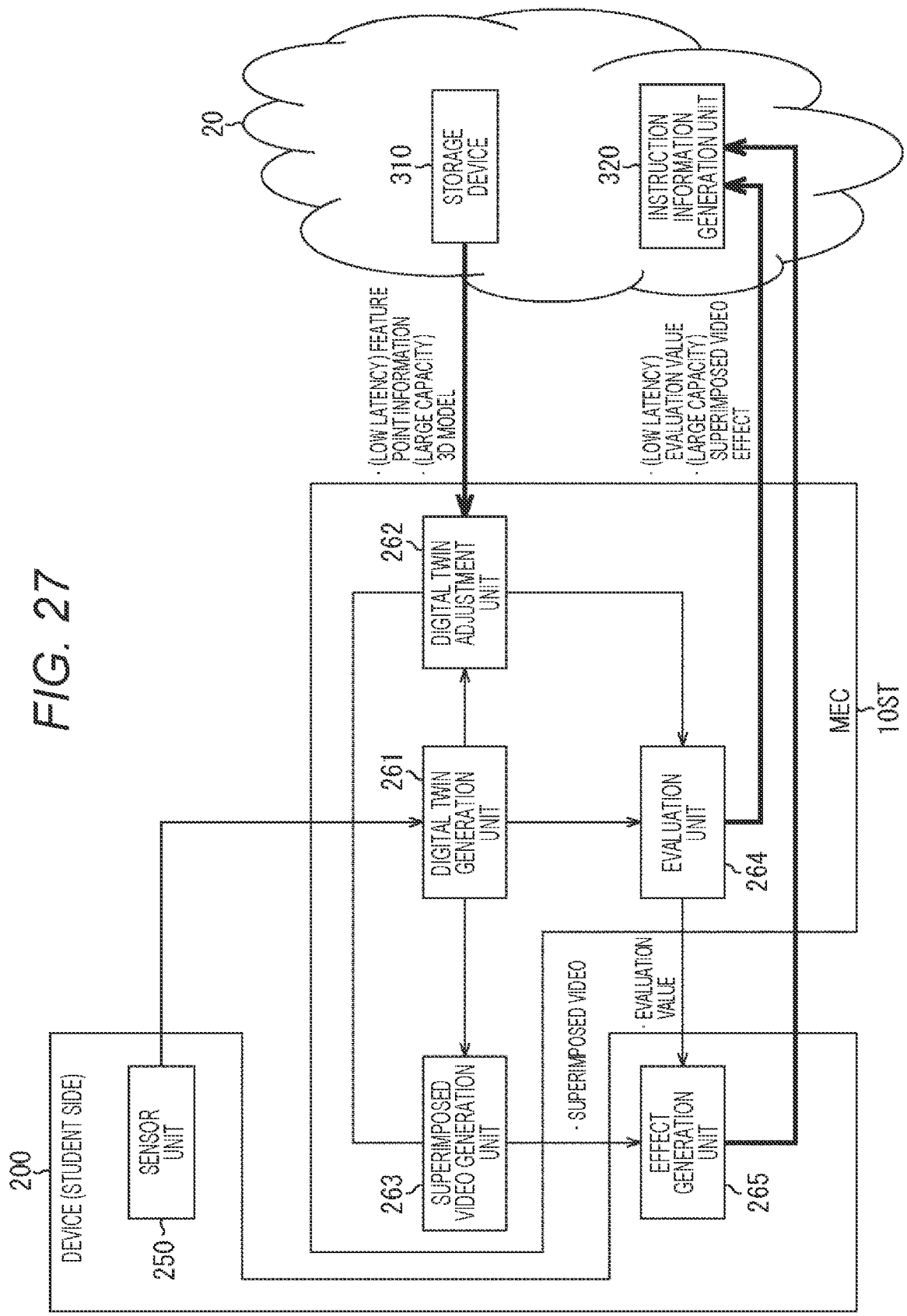
FIG. 27 is a diagram illustrating an application example of 5G network slicing.

As illustrated in FIG. 27, the digital twin generation unit 261 to the evaluation unit 264 may be implemented on the MEC server 10ST close to the device 200 on the student side.

In the example of FIG. 27, in the teacher digital twin stored in the storage device 310, from the cloud server 20 to the MEC server 10ST (the digital twin adjustment unit 262) on the student side, the feature point information is transmitted via a low latency slice, and the 3D model is transmitted via a large-capacity slice.

In addition, the evaluation value calculated by the evaluation unit 264 is transmitted from the MEC server 10ST on the student side to the cloud server 20 (the instruction information generation unit 320) via a low latency slice. Furthermore, from the device 200 on the student side to the cloud server 20 (the instruction information generation unit 320), the superimposed video generated by the superimposed video generation unit 263 and the effect video generated by the effect generation unit 265 are transmitted via a large-capacity slice.

Note that the superimposed video generated by the superimposed video generation unit 263 may be transmitted from the MEC server 10ST on the student side to the device 200 (the effect generation unit 265) on the student side via a large-capacity slice. Furthermore, the evaluation value (3D model information) calculated by the evaluation unit 264 may be transmitted from the MEC server 10ST on the student side to the device 200 (the effect generation unit 265) on the student side via a large-capacity slice.

(3-3-5. Device-MEC-Cloud Configuration 5)

Figure 28:
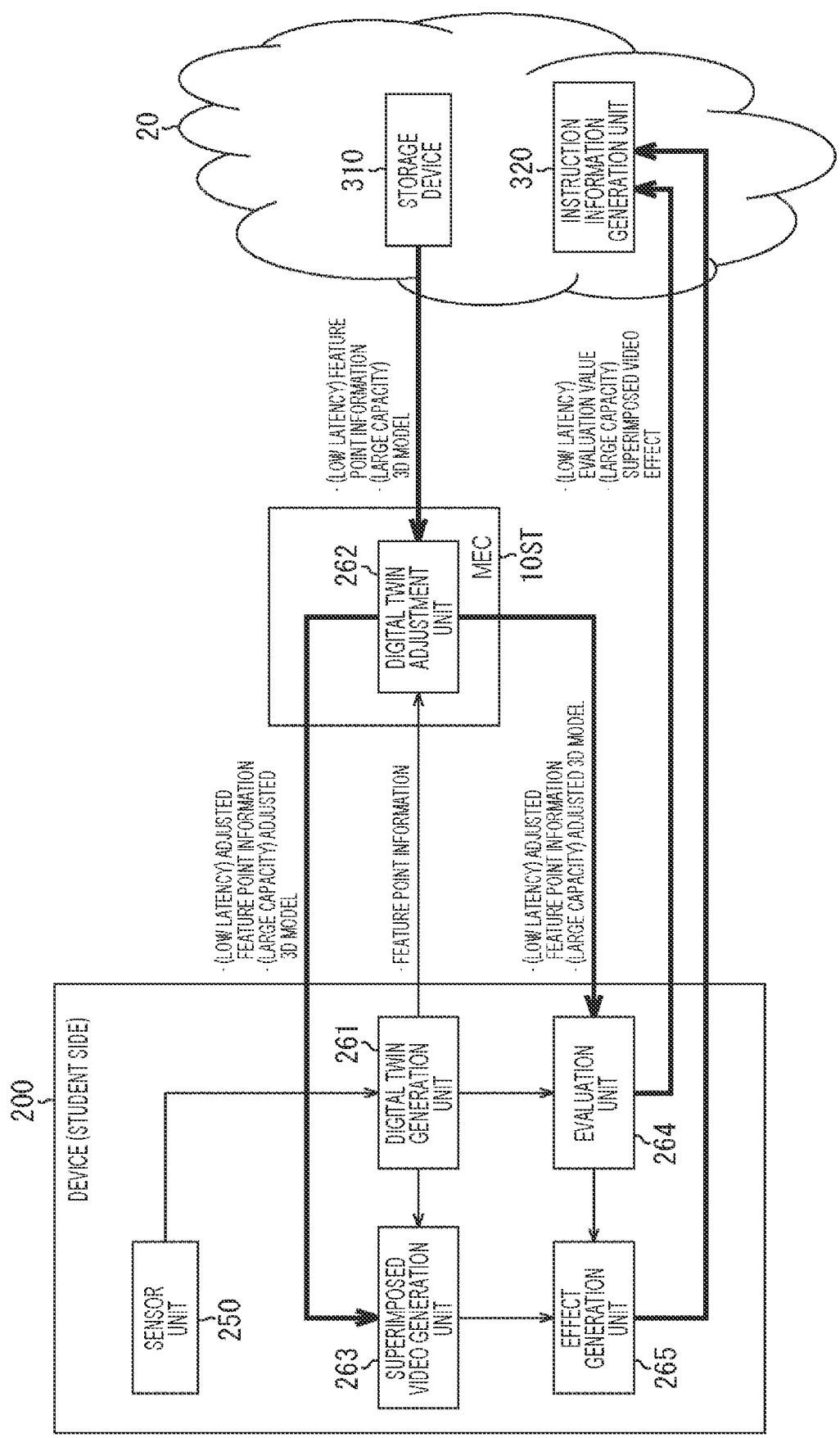
FIG. 28 is a diagram illustrating an application example of 5G network slicing.

As illustrated in FIG. 28, only the digital twin adjustment unit 262 may be implemented on the MEC server 10ST close to the device 200 on the student side.

In the example of FIG. 28, in the teacher digital twin stored in the storage device 310, from the cloud server 20 to the MEC server 10ST (the digital twin adjustment unit 262) on the student side, the feature point information is transmitted via a low latency slice, and the 3D model is transmitted via a large-capacity slice.

From the MEC server 10ST on the student side, to the device 200 (the superimposed video generation unit 263 and the evaluation unit 264) on the student side, among the adjusted teacher digital twin generated by the digital twin adjustment unit 262, the adjusted feature point information is transmitted via a low latency slice, and the adjusted 3D model is transmitted via a large-capacity slice.

Furthermore, from the device 200 on the student side to the cloud server 20 (the instruction information generation unit 320), the evaluation value calculated by the evaluation unit 264 is transmitted via a low latency slice, and the superimposed video generated by the superimposed video generation unit 263 and the effect video generated by the effect generation unit 265 are transmitted via a large-capacity slice.

Note that the feature point information of the student digital twin generated by the digital twin generation unit 261 may be transmitted to the teacher side (the digital twin adjustment unit 262) via a low latency slice.

As described above, the 5G network slicing can also be applied to the information processing system of FIG. 22.

4. Modifications

Hereinafter, modifications of the above-described embodiment will be described.

(Display Example of Digital Twin)

In the above description, as the digital twin, the 3D model combined with the skin data is displayed on the device 200 or the like on the student side. In addition, as illustrated in FIG. 29, the skeleton image based on the skeleton information may be superimposed and displayed on the 3D model as the digital twin.

Figure 29:
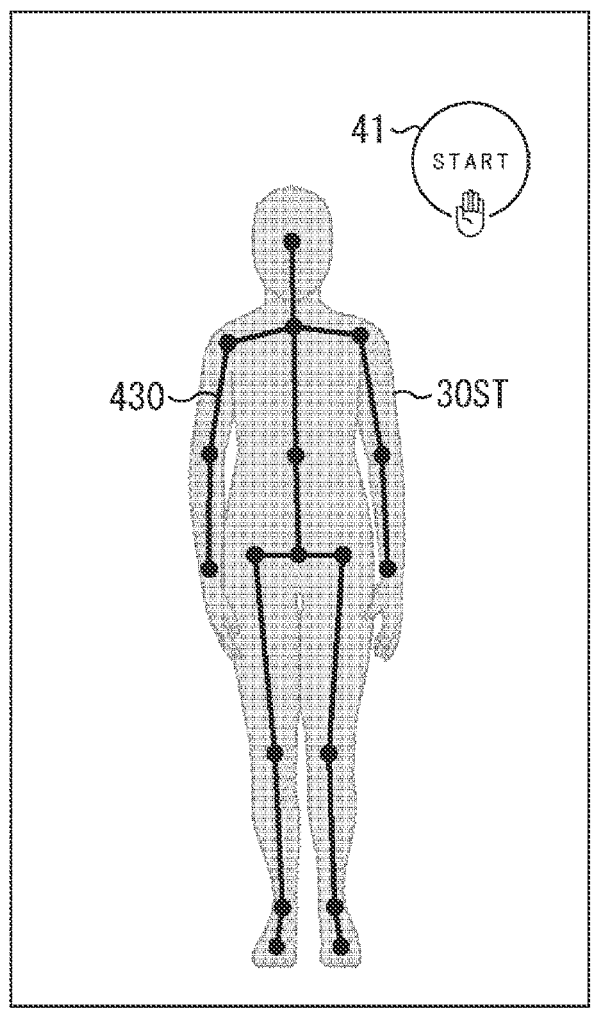
FIG. 29 is a diagram illustrating a display example of the digital twin.

In the example of FIG. 29, a skeleton image 430 representing a skeleton and joint points of a person who is a student is superimposed and displayed on an upright student digital twin 30ST (3D model). In the example of FIG. 29, the teacher digital twin 30TE illustrated in FIG. 2 is not superimposed, but the teacher digital twin 30TE may be further superimposed and displayed on the skeleton image 430.

(Presentation Example of Character Information)

In the above description, information such as a digital twin, instruction information, and an evaluation value is transmitted and received between the device 100 on the teacher side and the device 200 on the student side. In addition, for example, status information indicating the progress status of the lesson taken by the student and the state of the student performing the body motion in the lesson may be transmitted and received between the device 100 on the teacher side and the device 200 on the student side.

Figure 30:
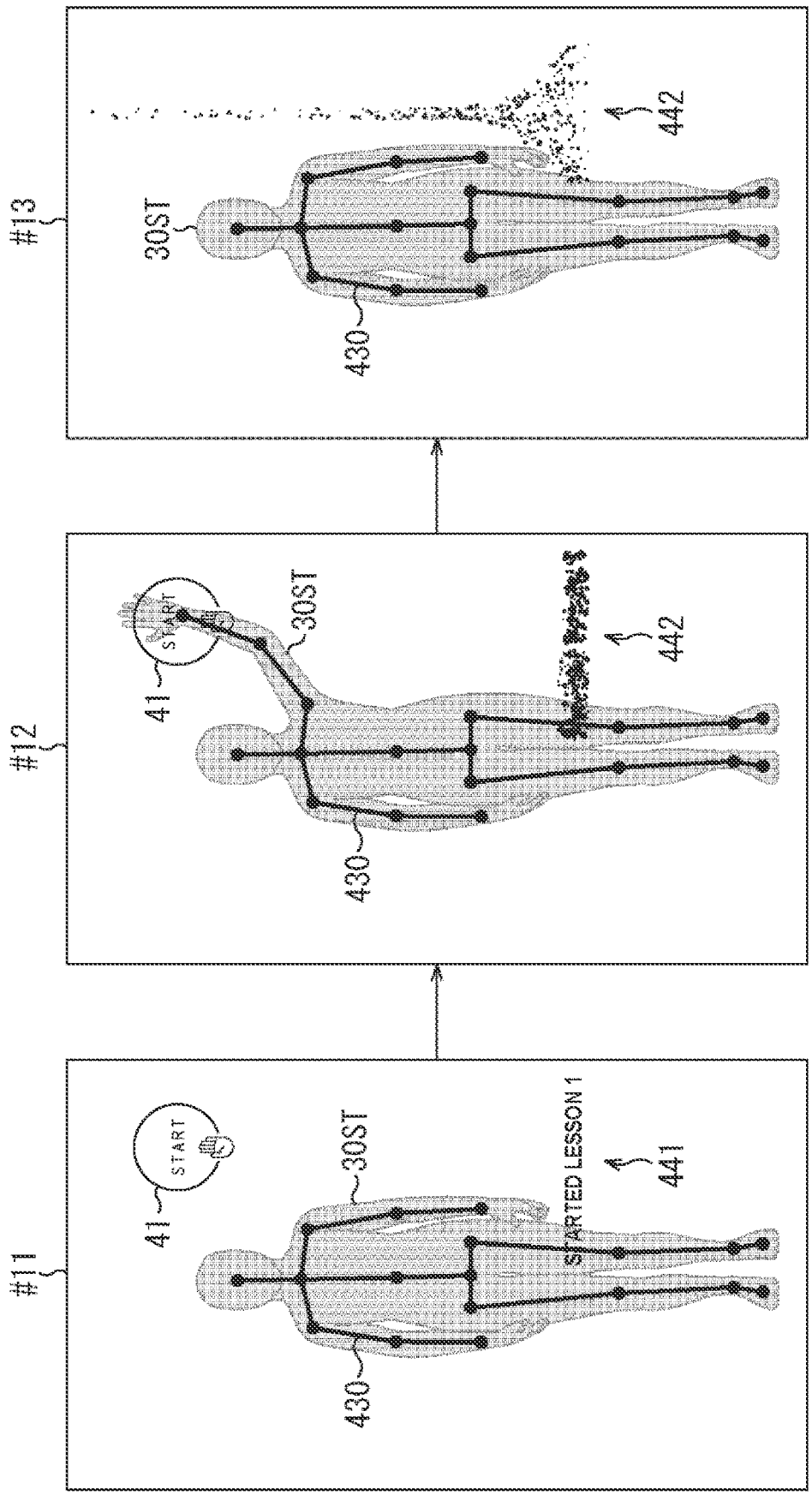
FIG. 30 illustrates a presentation example of character information.
Figure 31:
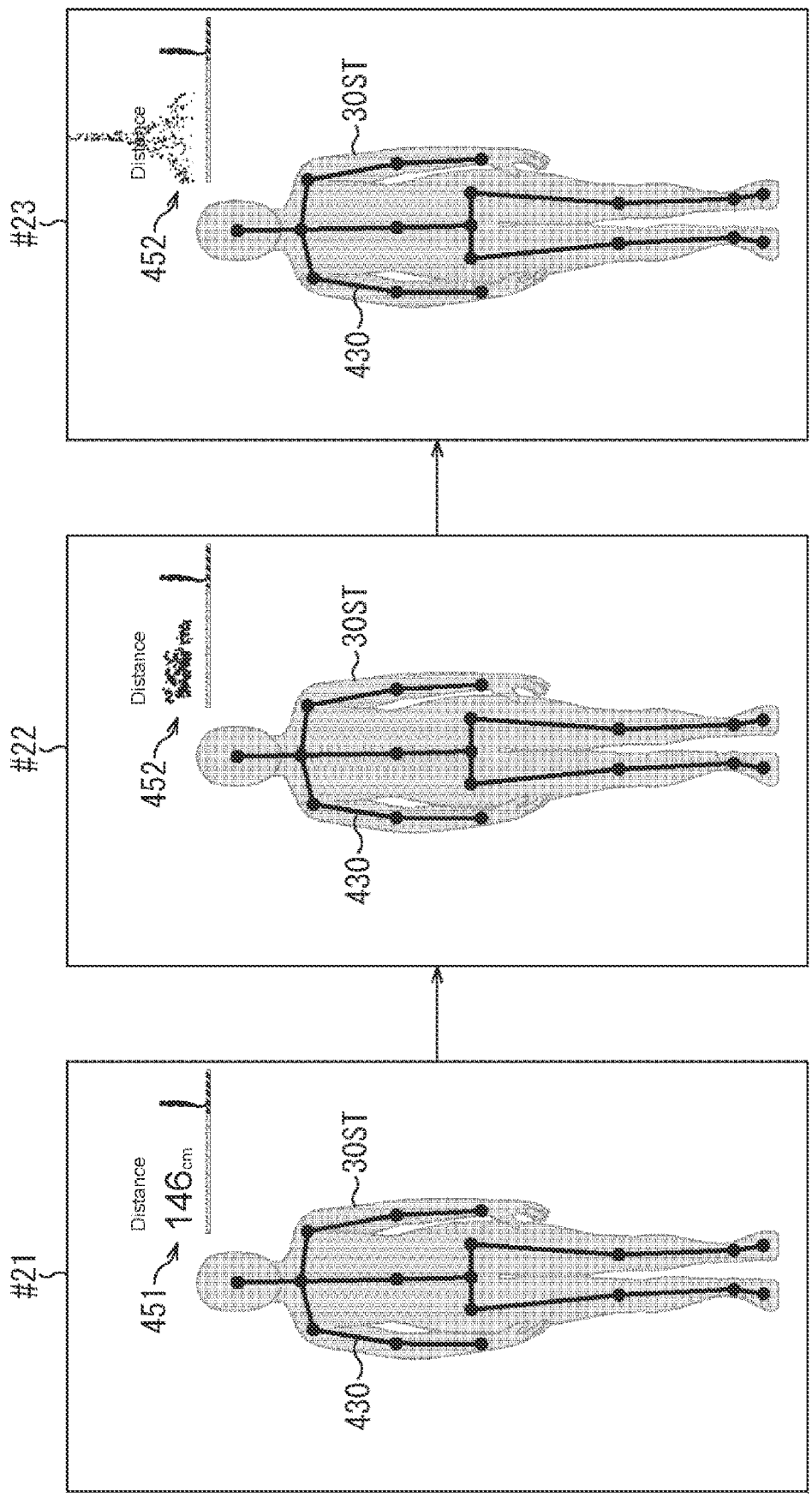
FIG. 31 illustrates a presentation example of character information.
Figure 32:
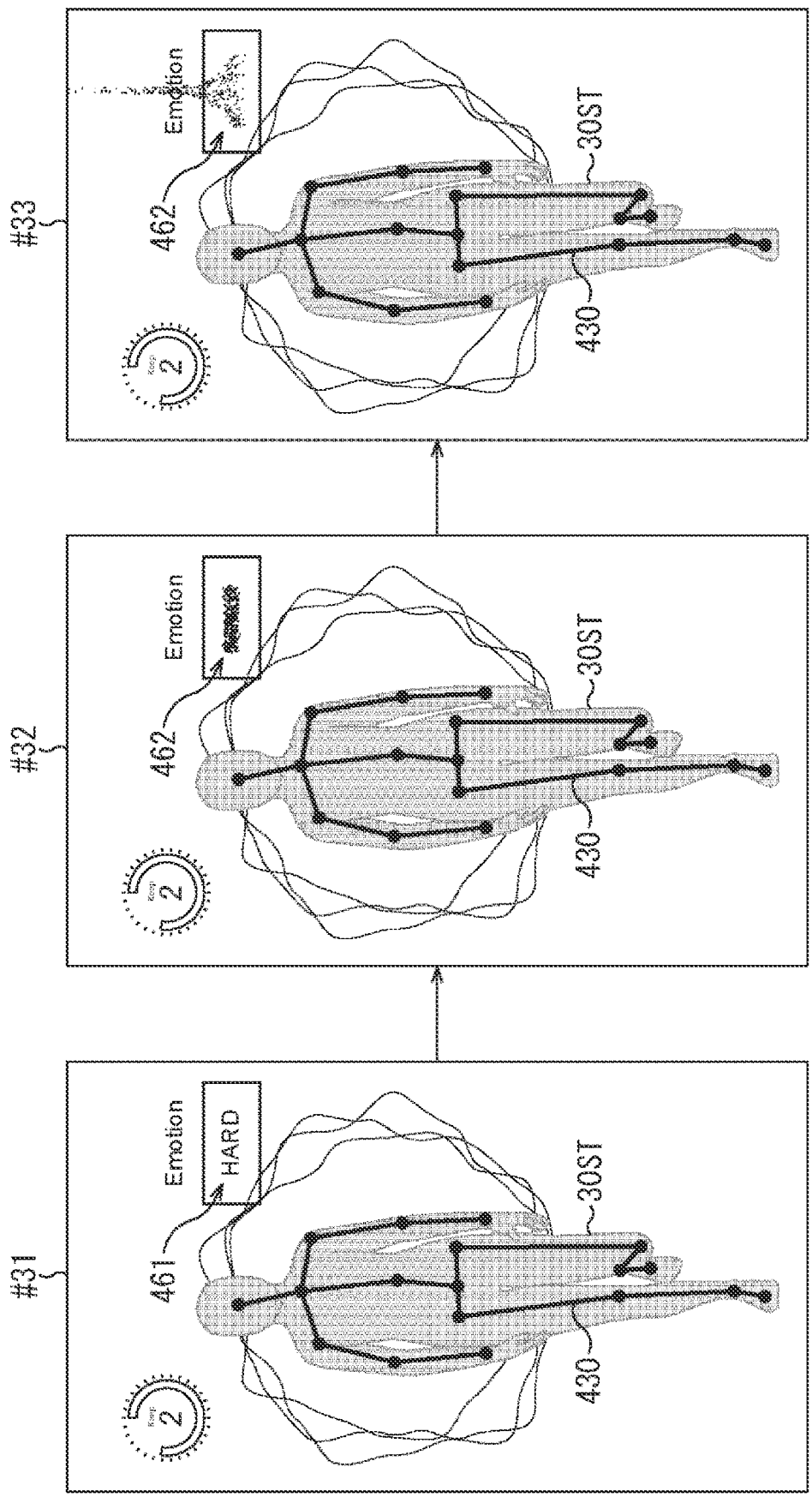
FIG. 32 illustrates a presentation example of character information.

FIGS. 30 to 32 are diagrams illustrating presentation examples of character information indicating the above-described status information in the device 200 on the student side.

Presentation Example 1

In the example of FIG. 30, status information indicating that a lesson is started by the student performing an operation for starting the lesson is transmitted from the device 200 on the student side to the device 100 on the teacher side.

For example, in the state of the screen #11 of FIG. 30, character information 441 indicating the name of a lesson to be started is displayed together with the student digital twin 30ST standing upright. Furthermore, on the upper right of the screen #11, a GUI button 41 for starting a lesson is displayed as in FIG. 2.

As illustrated in the state of the screen #12, if the student raises one hand and it is determined that the hand of the corresponding student digital twin 30ST overlaps the area of the button 41, the lesson by the instructor TE is started. At this time, the character information 441 changes to a particle video 442.

Thereafter, status information indicating the start of a lesson is transmitted to the device 100 on the teacher side, and the particles constituting the particle video 442 move so as to be sucked into the upper side of the screen #13 as illustrated in the state of the screen #13.

As described above, the character information 441 changes to the particle video 442 and moves to the upper side of the screen #13, so that the student as the user can intuitively understand that the status information indicating the start of the lesson has been transmitted to the device 100 on the teacher side.

Presentation Example 2

In the example of FIG. 31, status information indicating that the student taking a lesson is too close to the display (display unit 210) and is dangerous is transmitted from the device 200 on the student side to the device 100 on the teacher side.

For example, in the state of the screen #21 in FIG. 31, character information 451 indicating the distance between the student and the display is displayed together with the student digital twin 30ST. On the screen #21, the character information 451 indicates that the distance between the student and the display is 146 cm.

When the distance between the student and the display falls below a predetermined threshold value (for example, 145 cm), the character information 451 changes to the particle video 452 as illustrated in the state of the screen #22.

Thereafter, status information indicating the student is too close to the display is transmitted to the device 100 on the teacher side, and the particles constituting the particle video 452 move so as to be sucked into the upper side of the screen #23 as illustrated in the state of the screen #23.

As described above, the character information 451 changes to the particle video 452 and moves to the upper side of the screen #23, so that the student as the user can intuitively understand that the status information indicating the student himself/herself is too close to the display has been transmitted to the device 100 on the teacher side.

Presentation Example 3

In the example of FIG. 32, status information indicating that the physical load of the student taking a lesson is transmitted from the device 200 on the student side to the device 100 on the teacher side. The status information indicating the physical load of the student is generated on the basis of a vital sign acquired by a vital sensor provided as the sensor unit 250, for example.

For example, in the state of the screen #31 in FIG. 32, character information 461 indicating the physical load of the student is displayed together with the student digital twin 30ST. On the screen #31, the character information 461 indicates that the physical load state of the student is "HARD".

When the vital sign of the student exceeds a predetermined limit value, the character information 461 changes to a particle video 462 as illustrated in the state of the screen #32.

Thereafter, status information indicating the physical load of the student exceeds a predetermined limit value is transmitted to the device 100 on the teacher side, and the particles constituting the particle video 462 move so as to be sucked into the upper side of the screen #33 as illustrated in the state of the screen #33.

As described above, the character information 461 changes to the particle video 462 and moves to the upper side of the screen #33, so that the student as the user can intuitively understand that the status information indicating the physical load of the student himself/herself exceeds the limitation has been transmitted to the device 100 on the teacher side.

In the above-described examples, the character information indicating the progress status of the lesson or the state of the student is changed to the particle video, but a part of the skeleton image 430 superimposed and displayed on the student digital twin 30ST may be changed to the particle video.

For example, when the skeleton image 430 corresponding to the portion of the student digital twin which has moved differently from the teacher digital twin changes to the particle video, the student can recognize that he/she has made an erroneous movement.

Note that when the character information changes to the particle video, display colors may change, for example, the black character information may change to the red particle video.

Application Example

The above-described presentation example can also be applied to, for example, a configuration in which a line manager of a factory monitors the state of on-site production line workers individually. In this case, the line manager can collectively grasp the work situation, the physical load, the mental stress, and the like of the on-site worker, and if there is a possibility that the state of the site worker hinders the work, the line manager can immediately notify the management manager of the factory of the possibility.
(Application of Face Authentication)

In the embodiments described above, face authentication may be performed when starting a lesson or when starting work in a factory, for example. As a result, it is possible for a teacher to avoid offering a lesson to a wrong student, and it is possible for a line manager of a factory to easily grasp an attendance state of an on-site worker.
(Adjustment of Digital Twin)

In the embodiment described above, mainly on the basis of the student digital twin reflecting the body motion of the student who is the user (first person), the teacher digital twin is adjusted so that the teacher digital twin reflecting the body motion of the teacher who is the reference person (second person) matches the student digital twin. Conversely, the student digital twin may be adjusted on the basis of the teacher digital twin so as to match the student digital twin with the teacher digital twin, or the person to be reference (reference person) may be switched between the student and the teacher.

5. Configuration Example of Computer

The series of processes described above can be executed by hardware, and can also be executed in software. In the case of executing the series of processes by software, a program forming the software is installed on a computer. Herein, the term computer includes a computer built into special-purpose hardware, a computer able to execute various functions by installing various programs thereon, such as a general-purpose personal computer, for example, and the like.

Figure 33:
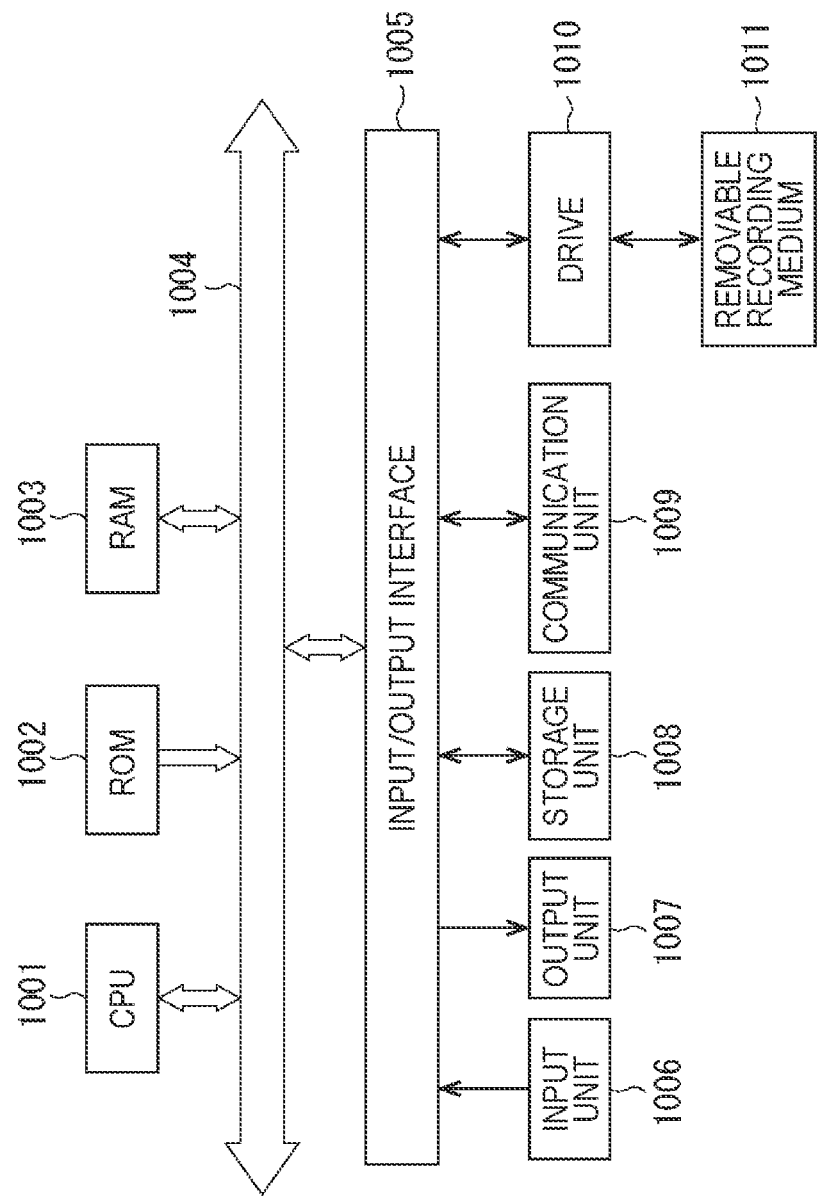
FIG. 33 is a block diagram illustrating a configuration example of a computer.

FIG. 33 is a block diagram illustrating a hardware configuration example of a computer that executes the series of processes described above according to a program.

In the computer, a central processing unit (CPU) 1001, read only memory (ROM) 1002, and random access memory (RAM) 1003 are interconnected by a bus 1004.

Additionally, an input/output interface 1005 is connected to the bus 1004. An input unit 1006, an output unit 1007, a storage unit 1008, a communication unit 1009, and a drive 1010 are connected to the input/output interface 1005.

The input unit 1006 includes a keyboard, a mouse, a microphone, and the like, for example. The output unit 1007 includes a display, a speaker, and the like, for example. The storage unit 1008 includes a hard disk, non-volatile memory, and the like, for example. The communication unit 1009 includes a network interface, for example. The drive 1010 drives a removable medium 1011 such as a magnetic disk, an optical disc, a magneto-optical disc, or semiconductor memory.

In a computer configured as above, the series of processes described above are performed by having the CPU 1001 load a program stored in the storage unit 1008 into the RAM 1003 via the input/output interface 1005 and the bus 1004, and execute the program, for example.

For example, programs to be executed by the computer (CPU 1001) can be recorded and provided in the removable medium 1011, which is a packaged medium or the like. In addition, the program can be supplied via a wired or wireless transmission medium such as a local area network, the Internet, or digital satellite broadcast.

In the computer, by mounting the removable medium 1011 onto the drive 1010, programs can be installed into the storage unit 1008 via the input/output interface 1005. Programs can also be received by the communication unit 1009 via a wired or wireless transmission medium and installed into the storage unit 1008. In addition, programs can be installed in advance into the ROM 1002 or the storage unit 1008.

Note that a program executed by the computer may be a program in which processing is chronologically carried out in a time series in the order described herein or may be a program in which processing is carried out in parallel or at necessary timing, such as when the processing is called.

In the present specification, steps of describing a program recorded in a recording medium include not only processing performed in chronological order according to the described order, but also processing executed in parallel or individually even if the processing is not necessarily performed in chronological order.

Further, in this specification, a system has the meaning of a set of a plurality of structural elements (such as an apparatus or a module (part)), and does not take into account whether or not all the structural elements are in the same casing. Therefore, the system may be either a plurality of apparatuses, stored in separate casings and connected through a network, or a single device including a plurality of modules within a single casing.

In addition, an embodiment of the present technology according to the present disclosure is not limited to the embodiments described above, and various changes and modifications may be made without departing from the scope of the technology according to the present disclosure.

Furthermore, the effects described in this specification are merely examples and are not limited, and other effects may be exerted.

Additionally, the technology according to the present disclosure may also be configured as below.

(1)

An information processing apparatus including:
  an adjustment unit configured to generate an adjusted second virtual object by adjusting, on the basis of feature point information of a first person included in a first virtual object reflecting a body motion of the first person, a second virtual object reflecting a body motion of a second person to be superimposed on the first virtual object.

(2)

The information processing apparatus according to (1), in which
  the adjustment unit changes the feature point information of the second person included in the second virtual object on the basis of feature point information of the first person included in the first virtual object.

(3)

The information processing apparatus according to (2), in which
the feature point information includes at least one of skeleton information, left and right information, or three-dimensional contour information.

(4)

The information processing apparatus according to any one of (1) to (3), in which
the adjustment unit adjusts at least a scale of the second virtual object on the basis of the feature point information.

(5)

The information processing apparatus according to any one of (1) to (4) further including
a generation unit configured to generate, on the basis of the feature point information of a person, a virtual object reflecting a body motion of the person.

(6)

The information processing method according to (5), in which
the generation unit extracts feature point information of the person on the basis of sensor data obtained by sensing the person.

(7)

The information processing apparatus according to (6), in which
the sensor data includes at least one of ToF data, RGB data, or volumetric capture data.

(8)

The information processing apparatus according to (6) or (7) further including
a sensor configured to sense the person.

(9)

The information processing apparatus according to (5), in which
the generation unit extracts the feature point information of the person on the basis of a video showing the person.

(10)

The information processing apparatus according to any one of (5) to (9), in which
the generation unit
removes a background of the person in the RGB data on the basis of the feature point information of the person and the RGB data obtained by sensing the person, and
generates the virtual object on the basis of the RGB data from which the background has been removed and the feature point information of the person.

(11)

The information processing apparatus according to any one of (5) to (10, in which
the generation unit generates the virtual object of a type according to a purpose of the body motion of the person.

(12)

The information processing apparatus according to any one of (1) to (11) further including
a video generation unit configured to generate a superimposed video in which the first virtual object is superimposed on the adjusted second virtual object.

(13)

The information processing apparatus according to (12) further including
an evaluation unit configured to generate an evaluation value of the first virtual object by comparing the first virtual object with the adjusted second virtual object.

(14)

The information processing apparatus according to (13), in which
the evaluation value includes at least one of a difference in three-dimensional contour information, a difference in acceleration information, or a difference in a predetermined fitting point between the first virtual object and the adjusted second virtual object.

(15)

The information processing apparatus according to (13) or (14) further including
an effect generation unit configured to generate an effect video for the superimposed video on the basis of the evaluation value.

(16)

The information processing apparatus according to (15), in which
the effect generation unit generates the effect video according to a purpose of the body motion of the first person.

(17)

The information processing apparatus according to (15) or (16) further including
a display control unit configured to display the superimposed video and the effect video on a display unit.

(18)

The information processing apparatus according to (17), in which
the display control unit switches the effect video to be displayed on the display unit according to an operation of the first person.

(19)

The information processing apparatus according to (17) or (18) further including
an instruction information generation unit configured to generate instruction information for the second person to provide a predetermined instruction to the body motion of the first person on the basis of the evaluation value.

(20)

The information processing apparatus according to (19), in which
the display control unit further displays the instruction information on the display unit.

(21)

The information processing apparatus according to any one of (1) to (20), in which
a virtual object includes feature point information of a person and a three-dimensional model based on the feature point information, and
the feature point information and the three-dimensional model are transmitted via different network slices.

(22)

The information processing apparatus according to (21), in which
the feature point information is transmitted via a low-latency network slice, and
the three-dimensional model is transmitted via a large-capacity network slice.

(23)

The information processing apparatus according to any one of (1) to (22), in which
a functional unit including the adjustment unit is implemented by a mobile edge computing (MEC).

(24)

The information processing apparatus according to any one of (1) to (23), in which the second virtual object is managed on the basis of copyright information including a person ID for specifying the second person.

(25) An information processing method including:
by an information processing apparatus,
generating an adjusted second virtual object by adjusting, on the basis of feature point information of a first person included in a first virtual object reflecting a body motion of the first person, a second virtual object reflecting a body motion of a second person to be superimposed on the first virtual object.

(26) A program causing a computer
to execute processing of:
generating an adjusted second virtual object by adjusting, on the basis of feature point information of a first person included in a first virtual object reflecting a body motion of the first person, a second virtual object reflecting a body motion of a second person to be superimposed on the first virtual object.

REFERENCE SIGNS LIST 10, 10TE, 10ST MEC Server
20 Cloud server
100 Device
150 Sensor unit
160 Control unit
161 Digital twin generation unit
162 Instruction information generation unit
200 Device
250 Sensor unit
260 Control unit
261 Digital twin generation unit
262 Digital twin adjustment unit
263 Superimposed video generation unit
264 Evaluation unit
265 Effect generation unit
266 Display control unit
310 Storage device
320 Instruction information generation unit
312 Storage unit
313 Control unit
1001 CPU

The invention claimed is:

1. An information processing apparatus, comprising:
circuitry configured to:
generate an adjusted second virtual object based on an adjustment of a second virtual object, wherein
the adjusted second virtual object is generated based on first feature point information of a first person included in a first virtual object,
the first virtual object reflects a body motion of the first person,
the second virtual object reflects a body motion of a second person,
the second virtual object is superimposed on the first virtual object,
the first virtual object includes
the first feature point information of the first person, and
a three-dimensional model of the first person based on the first feature point information, and
the first feature point information of the first person and the three-dimensional model of the first person are transmitted via different network slices.

2. The information processing apparatus according to claim 1, wherein
the circuitry is further configured to change second feature point information of the second person included in the second virtual object based on the first feature point information of the first person included in the first virtual object.

3. The information processing apparatus according to claim 2, wherein
the first feature point information includes at least one of skeleton information, left and right information, or three-dimensional contour information of the first person, and
the second feature point information includes at least one of skeleton information, left and right information, or three-dimensional contour information of the second person.

4. The information processing apparatus according to claim 2, wherein the circuitry is further configured to:
generate, based on the first feature point information of the first person, the first virtual object that reflects the body motion of the first person; and
generate, based on the second feature point information of the second person, the first virtual object that reflects the body motion of the second person.

5. The information processing apparatus according to claim 4, wherein the circuitry is further configured to:
extract the first feature point information of the first person based on sensor data corresponding to the first person; and
extract the second feature point information of the second person based on sensor data corresponding to the second person.

6. The information processing apparatus according to claim 5, wherein
each of the sensor data corresponding to the first person and the sensor data corresponding to the second person includes at least one of ToF data, RGB data, or volumetric capture data.

7. The information processing apparatus according to claim 4, wherein the circuitry is further configured to:
extract the first feature point information of the first person based on a first video that shows the first person; and
extract the second feature point information of the second person based on a second video that shows the second person.

8. The information processing apparatus according to claim 4, wherein the circuitry is further configured to:
generate the first virtual object of a first type based on a purpose of the body motion of the first person; and
generate the second virtual object of a second type based on a purpose of the body motion of the second person.

9. The information processing apparatus according to claim 1, wherein the circuitry is further configured to:
generate a superimposed video in which the first virtual object is superimposed on the adjusted second virtual object.

10. The information processing apparatus according to claim 9, wherein the circuitry is further configured to generate an evaluation value of the first virtual object based on a comparison of the first virtual object with the adjusted second virtual object.

11. The information processing apparatus according to claim 10, wherein
the evaluation value includes at least one of a difference in three-dimensional contour information, a difference in acceleration information, or a difference in a specific fitting point between the first virtual object and the adjusted second virtual object.

12. The information processing apparatus according to claim 10, wherein the circuitry is further configured to generate an effect video for the superimposed video based on the evaluation value.

13. The information processing apparatus according to claim 12, wherein the circuitry is further configured to control display of the superimposed video and the effect video on a display unit.

14. The information processing apparatus according to claim 13, wherein the circuitry is further configured to generate instruction information for the second person to provide a specific instruction to the body motion of the first person based on the evaluation value.

15. The information processing apparatus according to claim 1, wherein
the first feature point information is transmitted via a low-latency network slice, and
the three-dimensional model of the first person is transmitted via a large-capacity network slice.

16. The information processing apparatus according to claim 1, wherein
the second virtual object is managed based on copyright information including a person ID that specifies the second person.

17. An information processing method, comprising:
by an information processing apparatus,
generating an adjusted second virtual object based on an adjustment of a second virtual object, wherein
the adjusted second virtual object is generated based on first feature point information of a first person included in a first virtual object,
the first virtual object reflects a body motion of the first person,
the second virtual object reflects a body motion of a second person,
the second virtual object is superimposed on the first virtual object,
the first virtual object includes
the first feature point information of the first person, and
a three-dimensional model of the first person based on the first feature point information, and
the first feature point information of the first person and the three-dimensional model of the first person are transmitted via different network slices.

18. A non-transitory computer-readable medium having stored thereon, computer-executable instructions which, when executed by a computer, cause the computer to execute operations, the operations comprising:
generating an adjusted second virtual object based on an adjustment of a second virtual object, wherein
the adjusted second virtual object is generated based on first feature point information of a first person included in a first virtual object,
the first virtual object reflects a body motion of the first person,
the second virtual object reflects a body motion of a second person,
the second virtual object is superimposed on the first virtual object,
the first virtual object includes
the first feature point information of the first person, and
a three-dimensional model of the first person based on the first feature point information, and
the first feature point information of the first person and the three-dimensional model of the first person are transmitted via different network slices.

* * * * *